US008595302B2

(12) United States Patent
Krishnamurthi et al.

(10) Patent No.: US 8,595,302 B2
(45) Date of Patent: Nov. 26, 2013

(54) METHOD AND APPARATUS FOR MONITORING MESSAGE STATUS IN AN ASYNCHRONOUS MEDIATED COMMUNICATION SYSTEM

(75) Inventors: Govindarajan Krishnamurthi, Redwood City, CA (US); Stewart A. Skomra, Poway, CA (US); Srinivas Raghavan, San Diego, CA (US); Allan Schougaard, San Diego, CA (US); Deepa Suri, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 457 days.

(21) Appl. No.: 12/551,520

(22) Filed: Aug. 31, 2009

(65) Prior Publication Data

US 2010/0161743 A1 Jun. 24, 2010

Related U.S. Application Data

(63) Continuation-in-part of application No. 12/389,358, filed on Feb. 19, 2009.

(60) Provisional application No. 61/030,820, filed on Feb. 22, 2008.

(51) Int. Cl.
*G06F 15/16* (2006.01)

(52) U.S. Cl.
USPC ............ 709/206; 709/238; 709/239; 709/240

(58) Field of Classification Search
USPC .................................. 709/206, 238, 239, 240
See application file for complete search history.

(56) References Cited

U.S. PATENT DOCUMENTS

| 4,814,763 A | 3/1989 | Nelson et al. |
| 6,057,782 A | 5/2000 | Koenig |

(Continued)

FOREIGN PATENT DOCUMENTS

| EP | 1102443 A1 | 5/2001 |
| GB | 2323747 | 9/1998 |

(Continued)

OTHER PUBLICATIONS

International Search Report and Written Opinion—PCT/US2010/047298, International Search Authority—European Patent Office—Feb. 22, 2011.

(Continued)

*Primary Examiner* — Firmin Backer
*Assistant Examiner* — Jonathan Bui
(74) *Attorney, Agent, or Firm* — James T. Hagler

(57) ABSTRACT

A system and method for mediating the routing of asynchronous messages includes routing the asynchronous message to a first recipient, determining whether the first recipient opened the asynchronous message, and re-routing the asynchronous message to a second recipient who is qualified to receive and respond to the message if the first recipient fails to open the message (i.e., read, listen, display, act upon the message). In an embodiment, the message is re-routed to the second recipient if the first recipient fails to open the message within a deadline automatically imposed by the system when the message is of a certain type. In an embodiment, a mediator monitors if any recipient accepts responsibility for the asynchronous message and informs the other recipients that the asynchronous message may be deleted from their message queues.

34 Claims, 24 Drawing Sheets

(56) References Cited

U.S. PATENT DOCUMENTS

| | | | |
|---|---|---|---|
| 6,108,709 A * | 8/2000 | Shinomura et al. | 709/239 |
| 6,311,210 B1 | 10/2001 | Foladare et al. | |
| 6,854,007 B1 * | 2/2005 | Hammond | 709/206 |
| 7,093,025 B1 * | 8/2006 | Gupta | 709/239 |
| 7,363,344 B1 * | 4/2008 | Coletrane et al. | 709/206 |
| 7,370,278 B2 | 5/2008 | Malik et al. | |
| 7,707,260 B2 * | 4/2010 | Baratakke et al. | 709/206 |
| 8,149,850 B2 | 4/2012 | Krishnamurthi et al. | |
| 2002/0169855 A1 * | 11/2002 | Maehiro | 709/219 |
| 2002/0198999 A1 * | 12/2002 | Smith et al. | 709/227 |
| 2003/0131060 A1 * | 7/2003 | Hartselle et al. | 709/206 |
| 2004/0019695 A1 | 1/2004 | Fellenstein et al. | |
| 2004/0181586 A1 * | 9/2004 | Morreale et al. | 709/206 |
| 2005/0027803 A1 | 2/2005 | Kelley et al. | |
| 2005/0144246 A1 * | 6/2005 | Malik | 709/206 |
| 2005/0164681 A1 * | 7/2005 | Jenkins et al. | 455/412.1 |
| 2006/0212716 A1 * | 9/2006 | Ruddle | 713/186 |
| 2007/0005717 A1 * | 1/2007 | LeVasseur et al. | 709/206 |
| 2007/0011244 A1 * | 1/2007 | O'Neal et al. | 709/206 |
| 2007/0224979 A1 * | 9/2007 | O'Neal et al. | 455/417 |
| 2008/0016575 A1 * | 1/2008 | Vincent et al. | 726/26 |
| 2008/0034034 A1 * | 2/2008 | Agrawal | 709/203 |
| 2008/0104175 A1 * | 5/2008 | Keohane et al. | 709/206 |
| 2008/0148289 A1 | 6/2008 | Nicholls et al. | |
| 2008/0228888 A1 * | 9/2008 | Orozco et al. | 709/206 |
| 2008/0270545 A1 * | 10/2008 | Howe | 709/206 |
| 2008/0275953 A1 * | 11/2008 | Tanimoto | 709/205 |
| 2008/0281930 A1 * | 11/2008 | Hartselle et al. | 709/206 |
| 2009/0049134 A1 * | 2/2009 | Kumhyr et al. | 709/206 |
| 2009/0049139 A1 * | 2/2009 | Fouotsop et al. | 709/206 |
| 2009/0097631 A1 * | 4/2009 | Gisby et al. | 379/211.02 |
| 2009/0100497 A1 * | 4/2009 | Goldberg et al. | 726/1 |
| 2009/0132668 A1 * | 5/2009 | Coletrane et al. | 709/206 |
| 2009/0164637 A1 * | 6/2009 | Tanimoto | 709/226 |
| 2010/0042690 A1 * | 2/2010 | Wall | 709/206 |
| 2010/0057765 A1 * | 3/2010 | Dispensa et al. | 707/102 |
| 2010/0111275 A1 * | 5/2010 | Varma | 379/133 |
| 2010/0211638 A1 * | 8/2010 | Rougier | 709/205 |
| 2013/0041955 A1 * | 2/2013 | Chasin et al. | 709/206 |

FOREIGN PATENT DOCUMENTS

| | | |
|---|---|---|
| JP | 8314827 A | 11/1996 |
| JP | 9018375 A | 1/1997 |
| JP | H10240639 A | 9/1998 |
| JP | 11004251 A | 1/1999 |
| JP | 2000059422 A | 2/2000 |
| JP | 2002185535 A | 6/2002 |
| JP | 2003174481 A | 6/2003 |
| JP | 2004282655 A | 10/2004 |
| KR | 19980007265 A | 3/1998 |
| WO | WO9951048 | 10/1999 |
| WO | 2006071053 A1 | 7/2006 |
| WO | WO2009105607 | 8/2009 |

OTHER PUBLICATIONS

International Search Report and Written Opinion—PCT/US2009/034633, International Search Authority—European Patent Office—May 8, 2009.

* cited by examiner

| Role | Actor ID | Priority | Actor Address 1 | Actor Address 2 |
|---|---|---|---|---|
| Patient 1 | Dr. A | 1 | dra@hospital.com | 202-555-1212 |
| Patient 1 | Dr. B | 2 | drb@hospital.com | 202-555-1313 |
| Patient 1 | Dr. C | 3 | drc@hospital.com | 202-555-1414 |
| Patient 1 | Dr. D | 4 | drd@hospital.com | 202-555-1515 |
| Patient 1 | Nurse A | 5 | nursea@hospital.com | 202-555-1616 |
| Patient 1 | Nurse B | 6 | nurseb@hospital.com | 202-555-1717 |
| Patient 1 | Nurse C | 7 | nursec@hospital.com | 202-555-1818 |
| Patient 1 | PA A | 8 | paa@hospital.com | 202-555-1919 |
| Patient 1 | PA B | 9 | pab@hospital.com | 202-555-2121 |

FIG. 14a

| Role | Actor ID | Priority | Actor Address 1 | Actor Address 2 |
|---|---|---|---|---|
| Nurse | Nurse A | 1 | nursea@hospital.com | 202-555-1616 |
| Nurse | Nurse B | 2 | nurseb@hospital.com | 202-555-1717 |
| Nurse | Nurse C | 3 | nursec@hospital.com | 202-555-1818 |
| Nurse | Nurse D | 4 | nursed@hospital.com | 202-555-1919 |
| Nurse | Nurse E | 5 | nursee@hospital.com | 202-555-2121 |

FIG. 14b

| Actor ID | Status |
|---|---|
| Dr. A | Out |
| Dr. B | Out |
| Dr. C | Out |
| Dr. D | In |
| Nurse A | In |
| Nurse B | In |
| Nurse C | Out |
| Nurse D | Out |
| Nurse E | Out |
| PA A | Out |
| PA C | In |
| Admin A | Out |
| Admin B | Out |

FIG. 14c

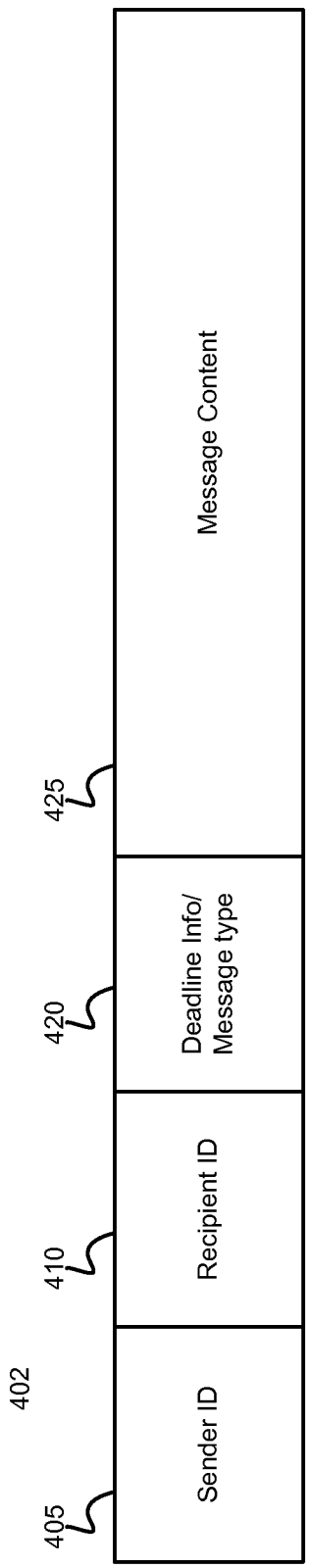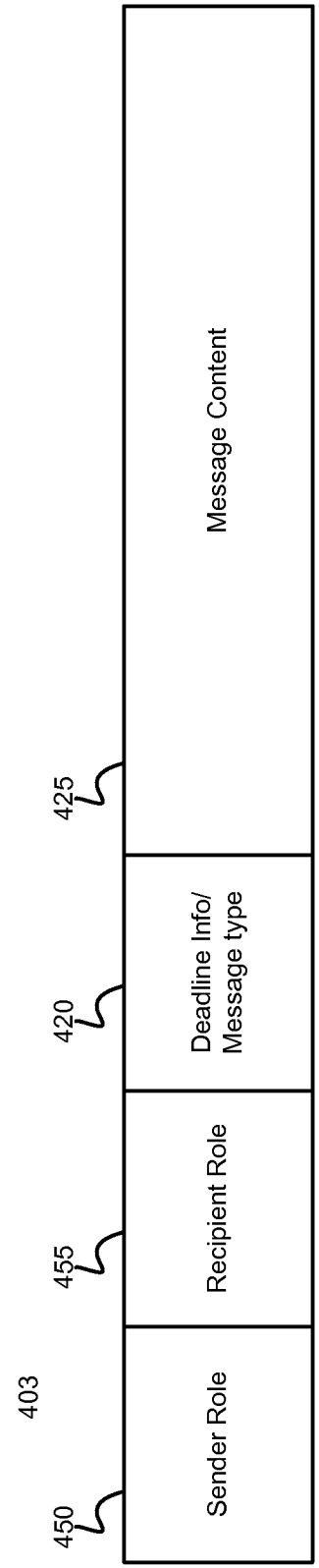

| Message Identifier | Original Recipient | Re-routed Recipient |
|---|---|---|
| 1 | Dr. A | Dr. B, Dr. C, Dr. D., Nurse A |
| 2 | Dr. A, Dr. B, Dr. C | Nurse A, Nurse B, Nurse C |
| 3 | PA A | Dr. A |
| 4 | Nurse B | Nurse A, Nurse C, Nurse D |
| 5 | Dr. A, Nurse A | Admin A |

FIG. 25

METHOD AND APPARATUS FOR MONITORING MESSAGE STATUS IN AN ASYNCHRONOUS MEDIATED COMMUNICATION SYSTEM

RELATED APPLICATIONS

The present application is a continuation in part of U.S. patent application Ser. No. 12/389,358 entitled "Method and Apparatus for Asynchronous Mediated Communication, filed Feb. 19, 2009 which claims the benefit of priority to U.S. Provisional Patent Application No. 61/030,829 filed Feb. 22, 2008, the entire contents of which are hereby incorporated by reference.

FIELD OF THE INVENTION

The present invention relates generally to computer communication technologies, and more particularly to a system and method for monitoring the status of asynchronous communication messages to avoid duplication of effort in responding to the asynchronous communication messages.

BACKGROUND

With the growth of e-mail and text messages (e.g., SMS messages) there is an on-going shift in mobile communications from synchronous communications to asynchronous communications. In this context, synchronous communications place the calling and called parties in direct communication during the exchange of information. Asynchronous communications occur when the calling party and called party are not in direct communication. Examples of popular asynchronous communication methods include Text Messaging, such as Short Messaging Service (SMS), multimedia messaging service (MMS), Electronic Mail (e-mail), Facsimile (fax), and numeric-only or alphanumeric paging (paging), voice mail, etc.

Asynchronous communication modes do not provide mechanisms to ensure that the intended recipient of a message will actually read, listen, display, act upon the message (i.e., open or play the message). At best, senders can request a read receipt, such as provided by most e-mail systems, or an acknowledgement that the message has been received. Additionally, current asynchronous communication modes do not rank the priority levels of sent messages. Using traditional e-mail as an example, flags may be set by senders to denote that the message is urgent. However, the recipient decides when to read the message. Consequently, in urgent situations some messages may not be read in time or read at all. These problems may limit the use of current asynchronous communication modes for communicating information with deadlines or urgent priority.

SUMMARY

Disclosed are communication systems, communication system components and methods for mediating the routing and re-routing of asynchronous messages. When asynchronous messages are sent in a communication network, message senders are provided tools with which they can prompt or ensure an action is taken and/or a reply is received in response to their asynchronous messages. The various embodiments re-route messages in the event the message is not acted upon or responded to within some threshold of time. Other embodiments monitor the status of re-routed asynchronous messages and insure that the asynchronous messages are removed from all recipient (original and re-routed) message queues once the asynchronous message has been acted upon by any recipient to avoid duplication of effort.

According to one embodiment, an asynchronous message is sent to a first recipient via a mediator and communication network. The mediator routes the message to the first recipient using routing information contained within the message, and re-routes the message to a second recipient based upon the role performed by the first recipient, and the relationship of the second recipient to the first recipient, if a message opened confirmation is not received from the first recipient. According to another embodiment, the message is re-routed to the second recipient if the message opened confirmation is not received within a deadline imposed by the sender. According to another embodiment, the message is re-routed to the second recipient, and potentially a third or more recipients, if the message opened confirmation is not received within a deadline automatically imposed based upon the type of message. Forwarding of the message to one or more additional recipients may be determined by the message content and situation or the enterprise environment. According to another embodiment, a reminder is sent to the first recipient if the message opened confirmation is not received within some period of time earlier than the deadline.

According to another embodiment, a reminder is sent to a second recipient if the message opened confirmation is not received from the first recipient within some period of time earlier than the deadline. The second recipient is selected based upon the role performed by the first recipient.

According to another embodiment, a mediator may monitor the status of an asynchronous message to determine if a message opened confirmation is received from any recipient (original or re-routed) that has received the asynchronous message. Once a message opened confirmation is received the mediator may take steps to delete the asynchronous message from all recipient queues to avoid duplicate responses to the asynchronous message.

According to another embodiment, a mediator may monitor the status of an asynchronous message to determine if any recipient (original or re-routed) has affirmatively accepted responsibility for the asynchronous message. Affirmative acceptance of responsibility for the asynchronous message may require more than simply opening the message. Affirmative acceptance of responsibility may require the recipient to affirmatively respond to either the sender or mediator indicating that the recipient is accepting responsibility for the message. Alternatively, the recipient may perform some action indicated in a nested action template which indicates that the recipient has accepted responsibility for the message or performed the action requested or required by the message. Once a recipient has accepted responsibility for the asynchronous message, the mediator may take steps to delete the asynchronous message from all recipient queues to avoid duplicate responses to the asynchronous message.

In another embodiment, the mediator may also indicate to users that messages have been deleted from their message queues.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain features of the invention.

FIG. 14a is an example of a static re-routing template of various actors performing the common role of healthcare for a particular patient.

FIG. 14b is an example of a static re-routing template of various actors performing a common role.

FIG. 14c is an example of a dynamic re-routing template which may be used in conjunction with a static re-routing template to determine alternative recipients of a message.

FIG. 15 is an example of a message structure for use in an embodiment method for insuring delivery of and action upon a sent message.

FIG. 16 is an example of a message structure for use in an embodiment method for insuring delivery of and action upon a sent message.

FIG. 25 is an example monitoring message data table.

DETAILED DESCRIPTION

Figure 1:
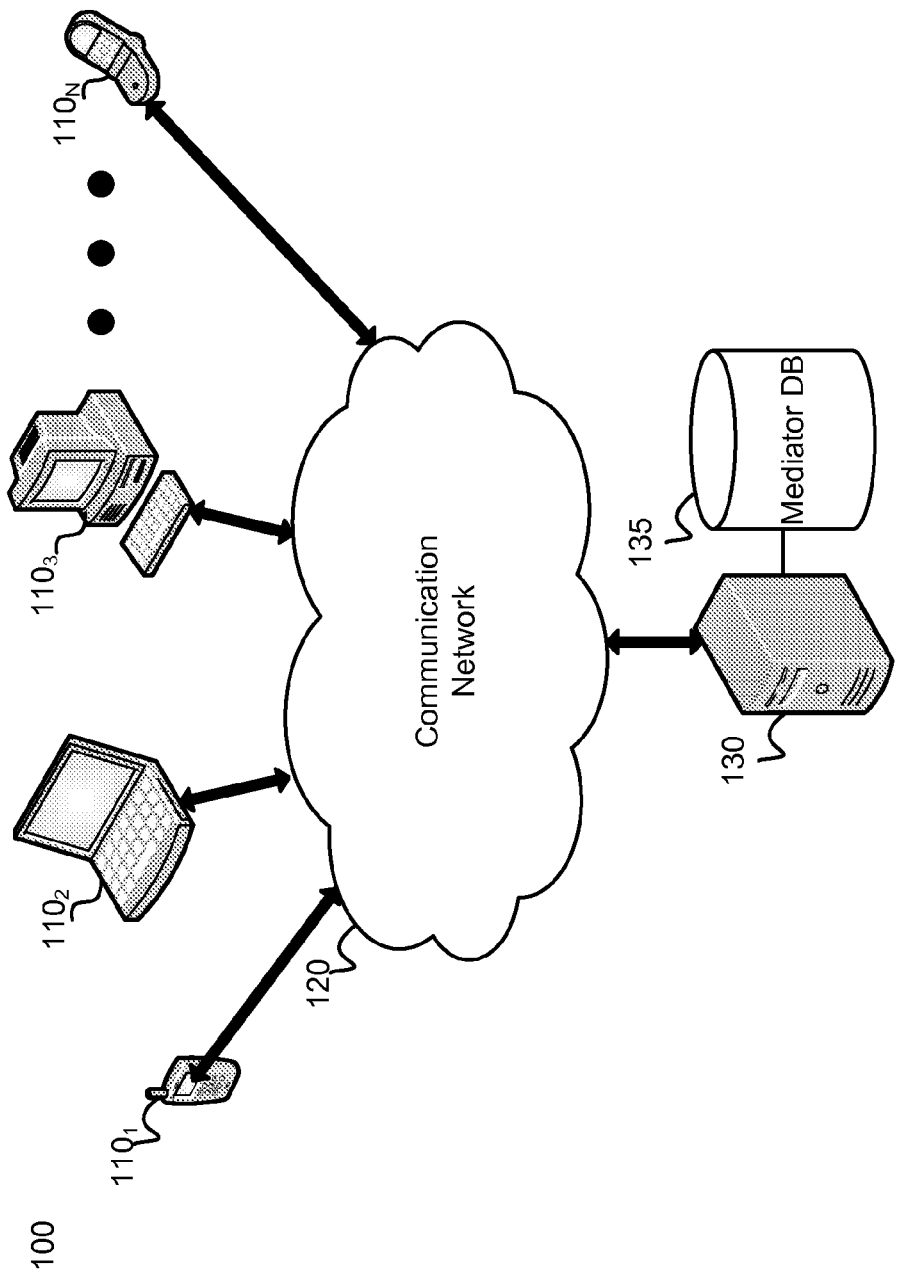
FIG. 1 is system block diagram of an example asynchronous mediated communication network.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

As used herein, the term "communication device" may refer to any one or all of cellular telephones, personal data assistants (PDA's), palm-top computers, laptop computers, desktop computers, wireless electronic mail receivers (e.g., the Blackberry® and Treo® devices), multimedia Internet enabled cellular telephones, and similar personal electronic devices which include a programmable processor and memory capable of sending and receiving at least one form of asynchronous message (e.g., SMS, MMS, IM (Instant Messaging), email, Facsimile (fax), voicemail, and numeric-only or alphanumeric paging (paging), etc.). In a preferred embodiment, the communication device is a cellular handset that can communicate via a cellular telephone network (e.g., a cellphone) and is capable of sending and receiving asynchronous type messages. However, the various embodiments are not intended to be limited to such communication devices and cellular telephone systems. Indeed the various embodiments may be implemented using any type of communication device linked to other communication devices via a communication network including desktop computers.

As used herein, the term "server" refers to any of a variety of commercially available computer systems configured to operate in a client-server architecture. In particular, the term "server" refers to network servers, particularly Internet accessible servers, which typically include a processor, memory (e.g., hard disk memory), and network interface circuitry configured to connect the server processor to the network, such as the Internet, an instant messaging network, a simple messaging system network and/or a cellular telephone network.

Recent technological advances have caused another shift in the communications paradigm. Despite the existence of conventional telephone and cellular telephone technology which allows users to reliably communicate synchronously over great distances, some users prefer to employ asynchronous modes of communication. Some observers point to the growth in the global connected community as a contributing factor to the communication paradigm shift. As users communicate with other users located in far off places in the world, differences in time zones often hamper synchronous communications. For example, finding a convenient time for a telephone call may be difficult when some participants are located in the United States and others are located in China. Asynchronous communication, such as email and SMS, is often more efficient since users can send and receive messages when it is most convenient for them without having to coordinate with others.

Despite the relative high degree of reliability of delivery afforded by modern asynchronous communication systems (e.g., text messages (SMS), e-mail, etc.), problems with asynchronous modes of communication persist. For example, while delivery of the message to a recipient's communication device may be confirmed, there are no mechanisms in place to ensure that the recipient user actually reads, displays, and/or plays (i.e., opens the message), and takes a prescribed action as a result of opening the message. For example, an e-mail may sit in a recipient's inbox for hours, days, even weeks before the recipient reads and responds to the email.

While the use of urgency flags, boldface type or other identifiers may be employed to inform the recipient of the relative importance of a message, the sender can do very little to prompt or ensure the recipient opens the message. Moreover, the sender can do little to prompt or ensure the recipient will act upon or respond to the original message within some imposed deadline.

This inability to elicit an action or response or enforce a deadline causes a lack of trust in asynchronous modes of communication for some participants and in some applications. This lack of trust and reliability of using asynchronous communication modes can cause significant problems for the sender and/or recipient.

In certain environments, prompt attention and response to messages may be of critical importance. For example, in the healthcare industry prompt receipt and response to messages or requests may have life or death consequences. As another example, in the legal industry briefs or other documents must be filed prior to strict filing deadlines. If instructions to file such documents are sent via asynchronous modes of communication (e.g., email), those sending the instructions could benefit from a mechanisms for ensuring that the action is completed within the deadline. As another example, family members coordinating child care duties via asynchronous modes of communication (e.g., email, SMS message, etc.) could benefit from mechanisms for ensuring a message is read and acted upon to ensure their children are picked up on time. Consequently, there is a need for systems and methods that ensure asynchronous messages are received and acted upon by a recipient even when the intended recipient is unavailable. Moreover, there is a need to provide a system and method to ensure that the asynchronous messages are received and acted upon before the expiration of critical deadlines.

Exploring the healthcare industry example further, most hospitals in the United States and elsewhere use both traditional synchronous and asynchronous modes for inter-clinician communication. In one example of a message flow, a physician who orders lab tests expects that the results will be reported back. In this example, the physician checks the patient, updates the patient's chart with the lab test order, and if needed, delivers the instructions to an assistant or nurse that the patient needs further testing at the lab. The assistant or nurse then places a work order for the lab to act on the samples taken from the patient, run the lab tests and report the results.

In one scenario, the samples from the patient are taken at the doctor's office. In another scenario, the patient goes to the lab or another medical department where the samples are taken from the patient. Once the lab has obtained the samples and the testing is completed, the lab technician conveys the test results to a nurse or assistant currently in charge of the patient's care. Depending on the urgency indicated by the physician's order or the test result (e.g., classified as critical, significant, or routine) the nurse or assistant may inform the doctor on-duty. The doctor, on seeing the lab results, then takes the next appropriate steps.

Using traditional synchronous or asynchronous communication modes, there are several communication nodes where communication breakdowns can occur. First, the sender and recipient of the communication may vary depending on who is on-duty when the message is communicated. For example, the physician who first orders the lab test may no longer be on duty when the lab test results are obtained. Similarly, the assistant or nurse who placed the lab order may be on a lunch break or off duty when the lab test results are conveyed back by the lab technician.

Second, a time lag may occur between the time the physician orders the lab test and the time the assistant or nurse places the lab test order. For example, the assistant or nurse may be busy with other patients and so cannot read the message (e.g., physician's lab test order) in a timely manner. Perhaps, the assistant or nurse is on a break. The assistant or nurse could be reassigned to other duties and not able to read the message. In some situations, the assistant or nurse may simply miss the physician's order. Thus, action on the message (e.g., lab test order) from the physician to the assistant or nurse may be delayed or missed altogether.

Third, a further time lag may occur between the time the lab test results are obtained and the time the physician receives the message conveying the lab results. For example, when the lab sends a message conveying the lab test results to the assistant or nurse who originally placed the lab test order, that assistant or nurse may no longer be on duty in which case the message may wait until he/she returns the next day. As another example, the lab technician may have to spend time determining the identity and contact information for the current assistant or nurse in charge of the patient before the message can be transmitted.

Fourth, based on the lab test results, the physician who ordered the lab tests needs to be informed but cannot be located or does not read the message promptly. For example, the physician may be off duty at the time, so the message waits until he/she is back on duty. As another example, the physician currently in charge of the patient may be too busy to read the message in a timely manner, so the message may end up in the physician's answering service. This causes further delays before the physician is informed of the message including the test results.

In each of these various communication breakdowns it would be desirable to take actions to ensure prompt delivery of and response to messages. Such actions may include alerting the recipient that the message (or response to the initial message) has been received, and prompting the recipient of a message to act upon or respond to the message. If the message cannot be timely delivered or is not responded to within a deadline, such action may include re-routing the message to another recipient qualified to receive the message. When re-routing a message it would be desirable to re-route the message to another recipient who is qualified to receive, act upon, and/or respond to the message. By doing so, the chances of obtaining an appropriate response to the original message are increased. In a similar manner in another embodiment the message may continue to be re-routed to a third, fourth or additional actors who fulfill the same role as the original intended recipient, if subsequent recipients do not respond in a timely manner to the message. Thus, the message may be re-routed to other actors who fulfill the same role as the original intended recipient.

A role may be a discrete job, a unit of work, or a functional responsibility within a multi-step process employed to achieve desired results with a given set of inputs. An individual's role may be determined by the individual's position within an asynchronous mediated communication (AMC) system. For example, in the healthcare industry, an individual's role may be one of administrator, physician, nurse, physician assistant, lab technician, affiliated hospital staff, etc. Alternatively, an individual's role may be determined by the individual's function within the AMC system. For example, in the healthcare industry, an individual's role may be emergency physician, oncology physician, radiologist, obstetrician, etc. Still further, an individual's role may be determined by the individual's responsibility within the AMC system. For example, in the healthcare industry, a recipient's role may be Patient XYZ treatment team member, Patient 123 treatment team member nurse, etc. Still further, an individual's role may be determined by a combination of position, function and/or responsibility as well as other parameters.

The individuals filling the roles may be referred to as actors, while actors may be people or system resources. For example, in the healthcare industry, actors may be the physicians, nurses, hospital staff, etc. Actors may also be the MRI machine, the CT scanner, the X-Ray, the radiation oncology device, etc. Still further, an actor may be a mediator 130 operating within the asynchronous mediated communication system 100 or within another asynchronous mediated communication system. Actors may also be information system services (i.e. agents) that are pre-programmed to receive, read, and respond to messages in the AMC system (e.g. a AMC Mediator service). Each of these resources fulfills a role in the AMC system to complete the multi-step communication process. Multiple actors may be assigned to a particular role. For example, in the healthcare industry, multiple individuals (i.e., actors) can perform the role of attending physician to a particular patient depending on the location, time of day and day of the week (e.g., the attending physician in the oncology ward of hospital branch #1 on Monday is a different individual than the attending physician on Tuesday). Further, a single actor may perform more than one role. For example, in the healthcare industry, an attending physician to a particular patient may also be the back-up physician for another patient.

The AMC system may be made aware of each actor through an enrollment process that provides the AMC system with information that is specific and unique to an individual actor. This information may include a User ID and Password and is extensible to include any details pertaining to the actor's identity and preferences. For example, the preferences may identify the different communication technologies (e.g., phone, e-mail, SIP address, etc.) that an actor would like to use for particular messaging types, the availability of an actor to fill specific or general categories of roles, other individuals who the actor prefers to interact with when filling an individual role, and the roles that the actor prefers to perform. The AMC system may create and maintain the actor's Identity (ID) information which may be used for the authentication, authorization and accounting (AAA) services of the AMC system. In an embodiment, the ID information comprises a "security" key pair (Private and Public) for use in the AAA services and with other mobile devices in the AMC system. In one example, the AAA services are performed by at least a processor in the AMC system. This processor may be contained within a mediator device/server. In one example, the processor is coupled to at least one memory for storage of the ID information. The memory may be local to the processor or located in a separate database.

As a consequence of the enrollment process, routing and re-routing templates (collectively referred to as routing templates) may be generated which assist in the routing and re-routing of asynchronous messages. A routing template for each possible role performed by all actors within an AMC system may be generated. By using information collected during the enrollment process routing templates may be populated with actors fulfilling the same roles as well as each actor's contact information and preferences. Alternatively, the routing templates may be in the form of separate but cross-correlated databases so that an actor role database, actor database, patient database and message routing rule database can be mapped one to another to achieve the message rerouting described herein. Additionally, the routing template may prioritize the listing of actors fulfilling the particular role. The priority listing may dictate the order in which actors are selected as routing or re-routing recipients of an asynchronous message.

While routing templates may be static, the actual order in which actors are selected as routing or re-routing recipients of an asynchronous message may dynamically change in accordance with an availability or status template. While an individual's assignment to various roles may be static, the actual roster of individuals fulfilling various roles may dynamically change by location as well as by the minute, hour, day, week, month, etc. For example, individual work schedules or attention to other projects/patients may force some actors to temporarily forgo their current duties, responsibilities, functions. As a result any message routed or re-routed to those actors may be ignored and thus require subsequent re-routing. In order to avoid this unnecessary delay a dynamic table of availability may be maintained by the mediator 130, or another device or database to which the mediator has access, to more efficiently route and re-route message.

Thus, in addition to static routing templates, dynamic availability templates may be generated and stored in a memory local to a processor or in a separate database. The dynamic availability template may track the availability of all actors within an AMC system in real time. As an example, the dynamic availability template may be linked with the administrative function of the AMC system that monitors when actors log in/out of the AMC system. Each time an actor logs into the AMC system via any communication device, the actor's status may change from "Out" to "In." Alternatively, as wireless communication devices associated during the enrollment process register with the AMC system's communication network, the corresponding actor's status may change from "Out" to "In" and vice versa. Alternatively, the dynamic availability template may be linked with a work schedule which may be manually updated. Other embodiments may employ any of a variety of methods to update the dynamic availability template. Examples of static role templates and dynamic availability tables are shown in FIGS. 14a-14c and described in more detail below with references to these figures.

In various embodiments, an original asynchronous message may be formulated based on a pre-determined message template. In one embodiment, a message template is chosen based on one or more of the following parameters: message content, actor, role, priority level, deadlines, etc. One skilled in the art would understand that other parameters (although not listed here) may be used to determine a message template chosen without affecting the spirit or scope of the present invention. The message template creates a structure for which a mediator may route and deliver the message to a recipient. In a healthcare industry example, a lab technician's template may indicate that a message regarding a particular blood test results should be sent to a patient's attending physician and nurse. Thus, if message type is identified as a blood test, the intended recipient may be explicitly identified but may also be identified by the role of the recipient. In the instant example, the role may be identified as attending physician or nurse, or possibly healthcare professionals attending to the identified patient. As discussed above, the message template may include an explicit deadline set by the message creator by which time a response to the message is required. Alternatively, a deadline may be automatically imposed for the message based upon the identified message type (e.g., blood test). Automatic deadlines may be further assigned according to message content. For example, a blood test for liver function may include a more pressing deadline than a blood test for a mild bacterial infection. Thus, by further defining the specific message type varying deadlines may be automatically imposed.

Depending on the role, certain actions may be taken by the actor fulfilling the role. In one embodiment, the action required by a message may be linked to particular roles using an action template. An action template is a database which includes a set of actions that the actor in that particular role may perform within the AMC system. Each action, in turn, may be associated with a set of rules that the mediator executes. The action template provides an easy to implement association of assigned or permissible actions to particular roles that the system can access in order to properly reroute a message in some circumstances. For example, an action template for the physician role may list permissible actions that a physician receiving a message including: initiate, delegate, escalate, add other actors, check status, etc. In contrast, the action template for the lab technician role may list permissible actions for a lab technician receiving the same message that are limited to escalate, add other actors, check status, etc., but preclude initiate or delegate.

Figure 26:
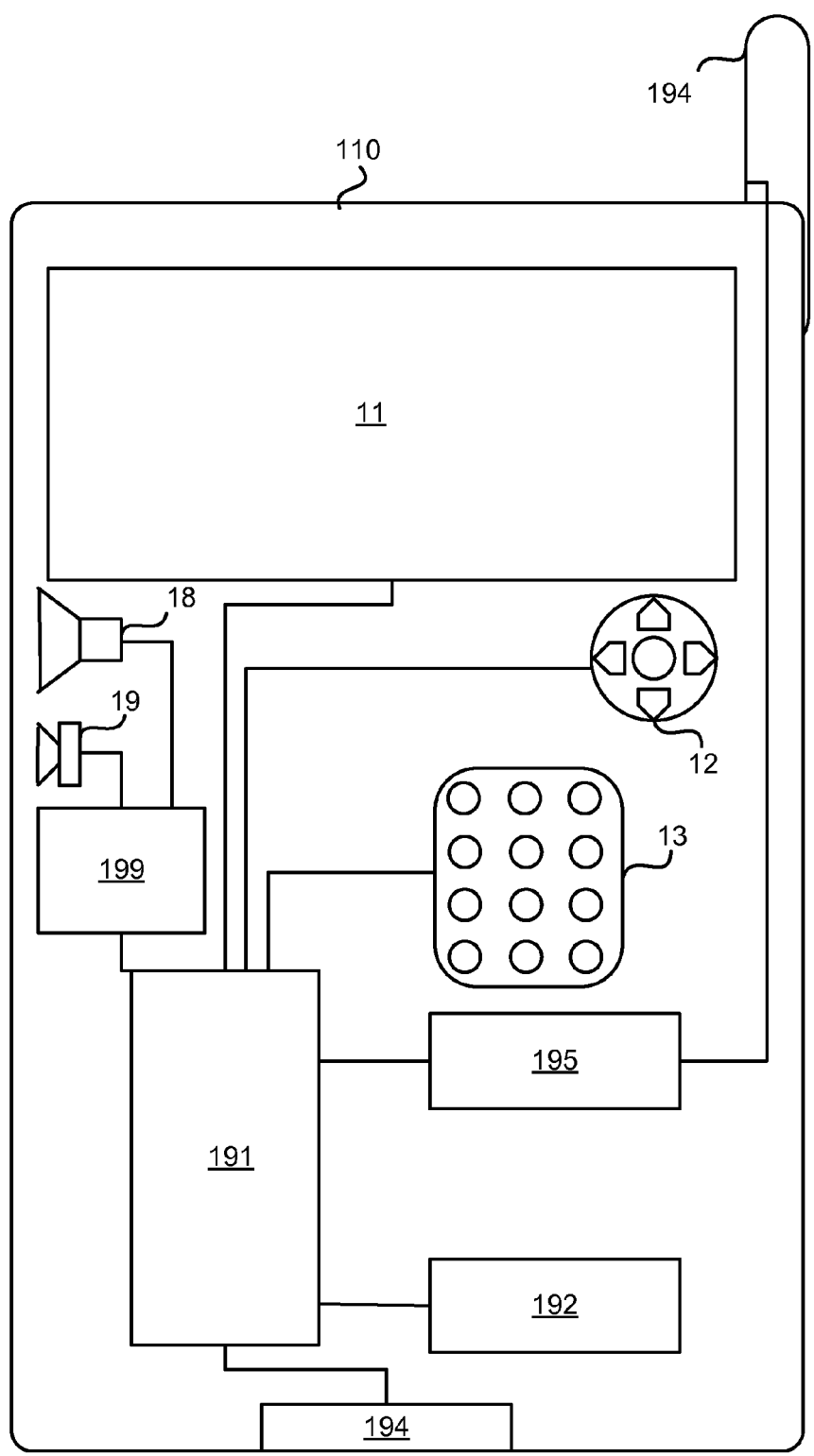
FIG. 26 a component block diagram of a communication device suitable for use with the various embodiments.

FIG. 1 is system block diagram of an example asynchronous mediated communication network system 100. The asynchronous mediated communication (AMC) system 100 comprises N mobile devices $110_1$, $110_2$, $110_3$ ... $110_N$, a communication network 120 and a mediator 130 between a sender and a recipient of a message. The mediator 130 may optionally be in communication with a mediator database 135. The mediator 130 provides message tracking and logging, thus ensuring a closed loop in the communication between the sender and recipient. In one embodiment, the mediator 130 may be a server device 210 and/or include a processor 361 coupled to a memory unit 362 (see e.g., FIG. 26). The mediator 130 may also be implemented as a distributed system in hardware and/or software in the network. Referring to FIG. 1, any one of the N mobile devices 110 can be a sender of a message, and similarly, any one or more of the rest of the N mobile devices 110 can be a recipient of that message. In one example, the message is sent from mobile device $110_1$ through the communication network 120 and mediator 130 to mobile device $110_2$. Communication network 120 may be a wireless or non-wireless network or a combination of both. One skilled in the art would understand that in some implementations of an AMC system 100, one or more of the mobile devices 110 could be replaced with a static device with access to a wired network without affecting the spirit or scope of the present invention.

In an alternative example asynchronous mediated communication network system, the communication devices $110_N$ may be interconnected with one another in the communication network system. Each of the individual communication device $110_N$ may contain a hardware and/or software capable of performing the functions of the mediator 130 described in the various embodiments herein.

Moreover, each communication device $110_N$ may be in communication with one or more asynchronous mediated communication network systems. Thus, each communication device $110_N$ may send and receive messages to different roles, actors, devices, according to different templates operating within different asynchronous mediated communication network systems.

Figure 2:
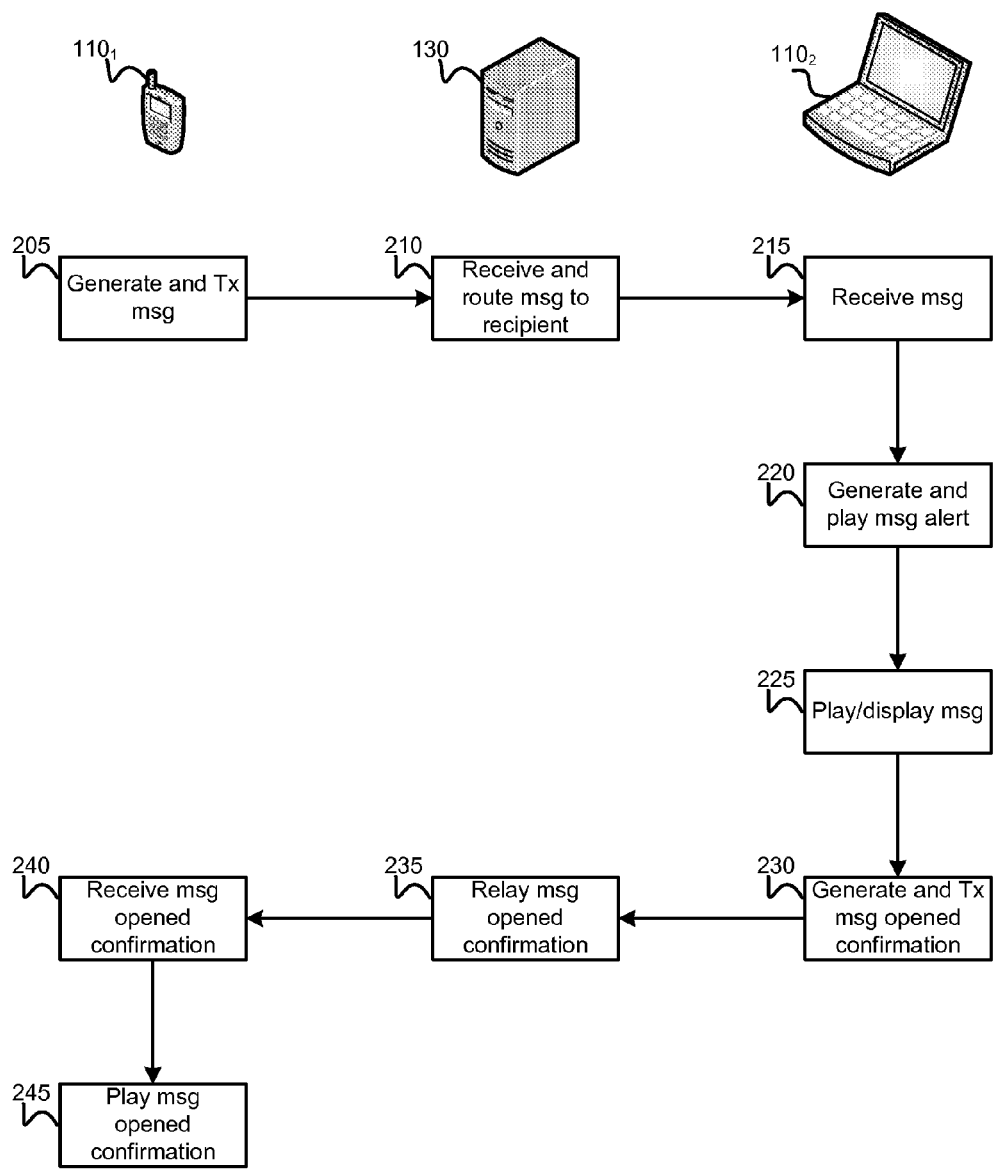
FIG. 2 is a process flow diagram of an embodiment method for providing a message delivery confirmation between two communication devices in an asynchronous mediated communication network.

FIG. 2 is a process flow diagram of an embodiment method for providing a message played/displayed confirmation between two communication devices (e.g., $110_1$ and $110_2$) in an AMC system 100. A sender using communication device $110_1$ generates and transmits a message to the mediator 130 for routing to a recipient using communication device $110_2$, step 205. The message is transmitted via a communication network 120 which interconnects communication devices $110_1$ and $110_2$ and mediator 130 such as illustrated in FIG. 1. The message may include the payload message as well as metadata which may assist in the routing and accurate delivery of the message. The mediator 130 receives the message from originating communication device $110_1$ and routes the message to $110_2$ using phone numbers, IP addresses or other identity parameters contained in the message metadata, step 210. The message is received by the recipient communication device $110_2$, step 215. In an embodiment, prior to opening the message (i.e., playing, displaying, reading and/or executing the message), the communication device $110_2$ may optionally generate and play and/or display a message alert notification to indicate that a message has been received, step 220. The message alert notification may be played/displayed in accordance with information included in the metadata, such as indicating the sender, an urgency level or a subject matter, for example. Once alerted, the recipient using communication device $110_1$ opens the message, step 225. When the message is opened the recipient's communication device $110_1$ may generate and transmit a message opened confirmation back to the originating sender's communication device $110_1$ via the mediator 130 and communication network 120, step 230. The message opened confirmation may indicate that the recipient who received and opened the message is taking responsibility to complete all of the prescribed actions that are required as a result of receiving and opening the message. The message opened confirmation may simply indicate that the recipient has received and opened the message. Alternatively, the message opened confirmation may also indicate that the recipient is taking the prescribed action as a result of receiving and opening the original message. In an alternative embodiment, the original received message may contain a nested action template within the message payload/content (see field 425 of FIGS. 10, 12, 15-18) which requests and generates a confirmation or series of confirmations as various prescribed action or series of actions are completed as a result of receiving and opening the original message. The nested action template may include time limits in which certain prescribed actions must be completed. Once a message is opened, the nested action template may trigger the mediator 130 to insure that the various prescribed action or series of actions are complete within any deadline. Otherwise, the mediator 130 may reroute the message in a manner similar to the process flow described below with reference to FIGS. 4-9.

The message opened confirmation is relayed to the originating sender's communication device $110_1$ by the mediator 130, step 235. The message opened confirmation is received by the originating sender's communication device $110_1$, step 240, after which the message opened confirmation may be played/displayed by the originating sender's communication device $110_1$, step 245. Playing/displaying the message opened confirmation informs the sender that the message has been received.

Figure 3:
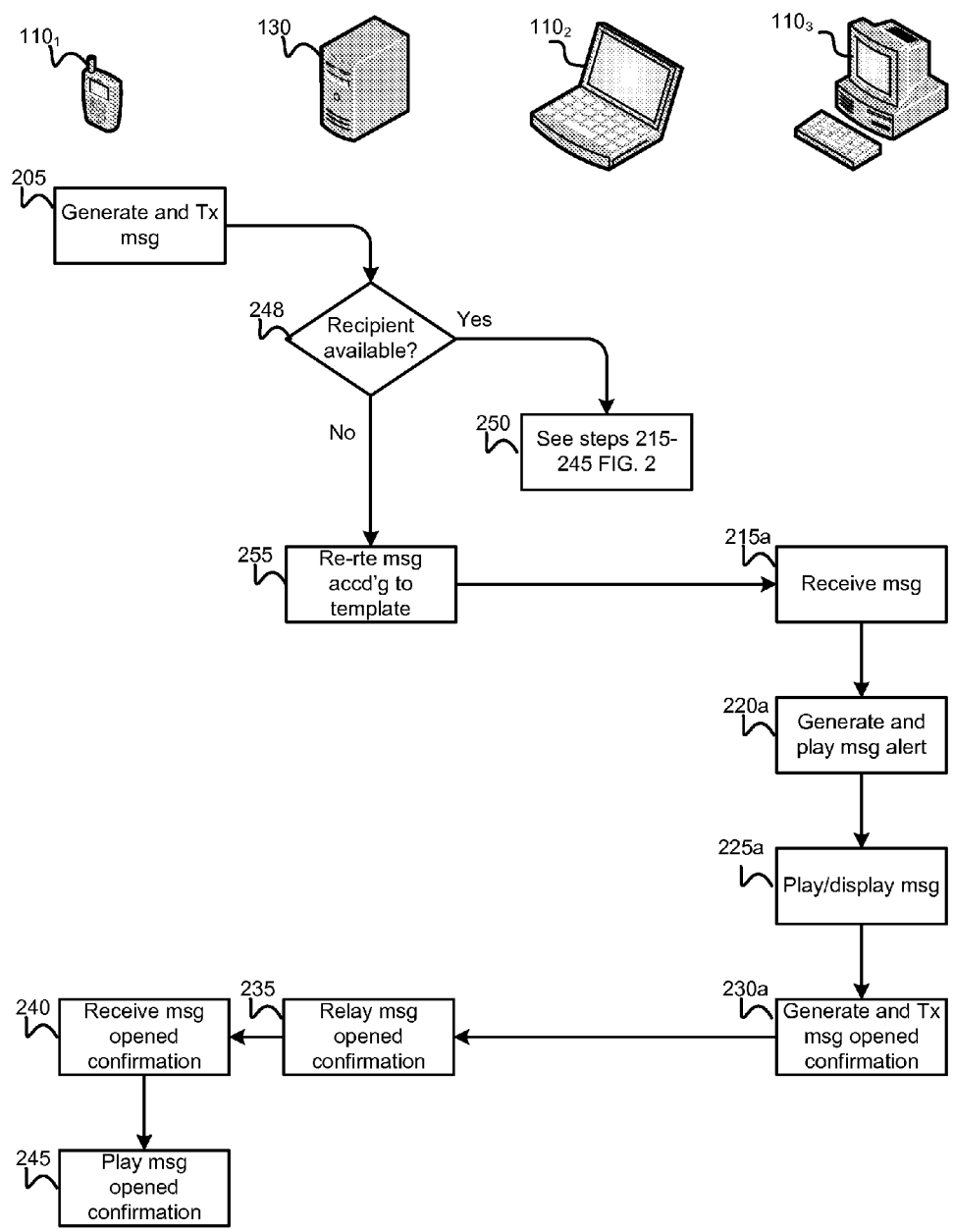
FIG. 3 is a process flow diagram of an embodiment method for re-routing a message when an intended recipient is unavailable in an asynchronous mediated communication network.

The process flow depicted in FIG. 2 illustrates an ideal situation in which the intended recipient is available and promptly receives and reads the message. However, this situation may not always be the case. FIG. 3 is a process flow diagram of an embodiment method for re-routing a message when the intended recipient is unavailable. By re-routing the message as soon as it is determined that the recipient not available, the embodiment method increases the chances that appropriate actions will be taken in response to the message.

In the process flow of FIG. 3, the sender using communication device $110_1$ generates and transmits a message to the mediator 130 for routing to a first recipient addressed to that recipient's communication device $110_2$, step 205. Upon receiving the message the mediator 130 may determine if the intended first recipient's communication device $110_2$ is available, decision 248. There may be a variety of reasons why the intended first recipient's communication device $110_2$ is not available. For example, intended first recipient's communication device $110_2$ may be turned off, logged off the network, out of range of the network, or out of power. Alternatively, the intended first recipient may simply be away from his/her communication device $110_2$ or busy attending to other matters or other messages. In order to determine whether the intended recipient is available or not the mediator 130 may allow some pre-determine period of time to elapse before determining that the first recipient is unavailable. By doing so, the mediator 130 allows the first recipient some window of time to receive and respond to the message.

If the intended first recipient's communication device $110_2$ is available (i.e., decision 248=Yes), then steps 215-245 of FIG. 2 may be performed. However, if the intended first recipient's communication device $110_2$ is not available (i.e., decision 248=No), mediator 130 may attempt to re-route the message in accordance with a routing template, step 255. This re-routing step and the routing template are described in greater detail below with reference to FIGS. 12-17. The purpose of re-routing the message in accordance with the re-routing template is to insure that the message is sent to another actor qualified to receive and act on/respond to the message. For example, if the message is a lab result intended for the doctor treating a patient, the appropriate role may be any other doctor capable of reading the lab result and acting upon the results appropriately. In such a case, the re-routing template may identify other doctors available to receive the message. In this example, the role of the recipient may be position dependent (i.e., doctor vis-à-vis nurse). By accurately identifying the role of the intended first recipient, messages may be re-routed in an efficient manner to increase the chances of eliciting a proper response to the message.

In some cases the appropriate role for re-routing a message may be responsibility of the dependent. For example, some patients may have a unique medical history such that only those medical professionals with knowledge of the patient's history are qualified to receive and act upon the lab results. Thus, it may be the case that a nurse or physician assistant may be more qualified to act upon and/or respond to the message than another doctor not familiar with the patient's medical history. Therefore, the message may be re-routed to someone who is part of the team treating a particular patient.

As part of or after routing (or re-routing) of the asynchronous message, the mediator 130 may establish a monitored message table data entry which maintains a listing of all recipients (original and re-routed) of the asynchronous message. Using such a data table, once a message opened confirmation is received by the mediator 130 from any of the recipients, the mediator 130 may inform the remaining recipients (i.e., recipients who received the asynchronous message but have not opened it) of the message opened confirmation and direct their communication devices 110 to delete the asynchronous message from their message queues to avoid duplicate responses to the asynchronous message. Various embodiment methods for monitoring asynchronous message status and avoiding duplicate responses are described in more detail below with reference to FIGS. 20-25.

If the message is re-routed according to the routing template, then the re-routed second recipient's communication device $110_3$ may receive the message and process it in a manner similar to that described above with reference to steps 215-230 of FIG. 2 (see step 215a-230a). As with the process flow shown in FIG. 2, once the message opened confirmation (or affirmative indication of acceptance of responsibility) is generated and transmitted (step 230a), it is relayed by the mediator 130, and received and played by the sender's communication device $110_1$ in the same manner as shown in FIG. 2.

Additionally, when the message opened confirmation (or affirmative indication of acceptance of responsibility) is received for relay by the mediator 130, the mediator 130 may determine if the message opened confirmation is for an asynchronous message having multiple recipients. If the received message opened confirmation is for an asynchronous message that has multiple recipients (original and/or re-routed), the mediator 130 may implement steps to delete the original and re-routed asynchronous messages from all of the recipient's (original and re-routed) message queues to avoid duplicate responses and a duplication of effort in responding to the asynchronous message. Various embodiments to monitor asynchronous message status and avoid duplicate responses to asynchronous messages are described in more detail below with reference to FIGS. 20-25.

In other embodiments (not shown), re-routing of messages may be performed manually. In such embodiments the mediator 130 may notify the sender that the intended recipient is unavailable. By doing so the sender may re-formulate the original message with a new intended recipient identified. Manual message redirection can include delegation to, transfer, or assigning of responsibility to another recipient and/or role. In one aspect, although the responsibility is transferred to another role, accountability may remain with the initial intended recipient. Manual message redirection may also include escalation to forward a message to other roles (e.g., appropriate personnel) that are authorized to make a decision, such as when the initial recipient is not able to make a decision based on the message content.

In the healthcare industry, delegation and escalation are actions that are required often. As an example of delegation, a physician in charge of a large number of patients may be unable to take care of all of them at a time when a critical decision needs to be made. In this case, the physician can delegate some of his patients' care to other caregivers. Thus, in this example, all messages related to delegated patients may be routed to the designated caregivers. In one aspect, the physician may choose to also receive or choose to not receive such messages. In another aspect, the physician may choose to receive selected messages based on message content, but not receive other messages while all messages (regardless of message content) are routed to the other caregivers.

As an example of escalation, a physician may not be able to make a decision based on the message content. In this situation, the AMC system 100 through the mediator 130 may escalate the message to a different actor by resending the message to another role (for example, a supervising physician) for a decision. Thus, the message initially sent to communication device $110_2$ of the physician may be resent to communication device $110_3$ of the supervising physician with an alert notification to be presented by the alert notification block 220a.

It may also be the case that the intended first recipient's communication device $110_2$ is available and receives the message while the first recipient is away or busy attending to other matters. In this case, the message was delivered to the communication device but is not read or acted upon by the intended recipient. Confirmation of delivery may not be sufficient if the sender requires a response to the original message within some deadline. For example, in the healthcare environment, an emergency room physician may send a trauma patient's head CT to a radiologist via email for immediate analysis and report. Because the patient is in the emergency room the emergency room physician may request that this head CT be given priority and read within five minutes. Therefore, if a message opened confirmation (indicating that the radiologist has received the CT scan and is in the process of formulating an analysis) is not received by the mediator 130 at some time prior to the expiration of the five minute deadline, the mediator 130 may re-route the message to another actor fulfilling the radiologist role.

In an alternative embodiment, a deadline for response may be automatically imposed on certain types of messages regardless of whether the sender imposes one or not. For example, the mediator 130 may be programmed to recognize messages containing a head CT scan or messages from the emergency room, and automatically impose a pre-determined deadline for response to the message. By doing so, if the emergency room doctor in haste forgets to impose a deadline, the AMC system can automatically re-route the message if a response is not received within the automatically imposed deadline.

Thus, in the emergency room example, if the intended radiologist has not read the head CT message and sent back a confirmation that the analysis is being performed within, for example, two minutes of the head CT being sent, the mediator 130 may re-route the message to another radiologist (i.e., another actor fulfilling the appropriate role). The original intended radiologist may be busy with another emergency room patient's CT and therefore cannot review the next incoming CT. If the original intended radiologist does not confirm that the CT was read within a threshold time before the deadline, the CT may be re-routed to another radiologist with enough time to meet the original deadline.

Figure 4:
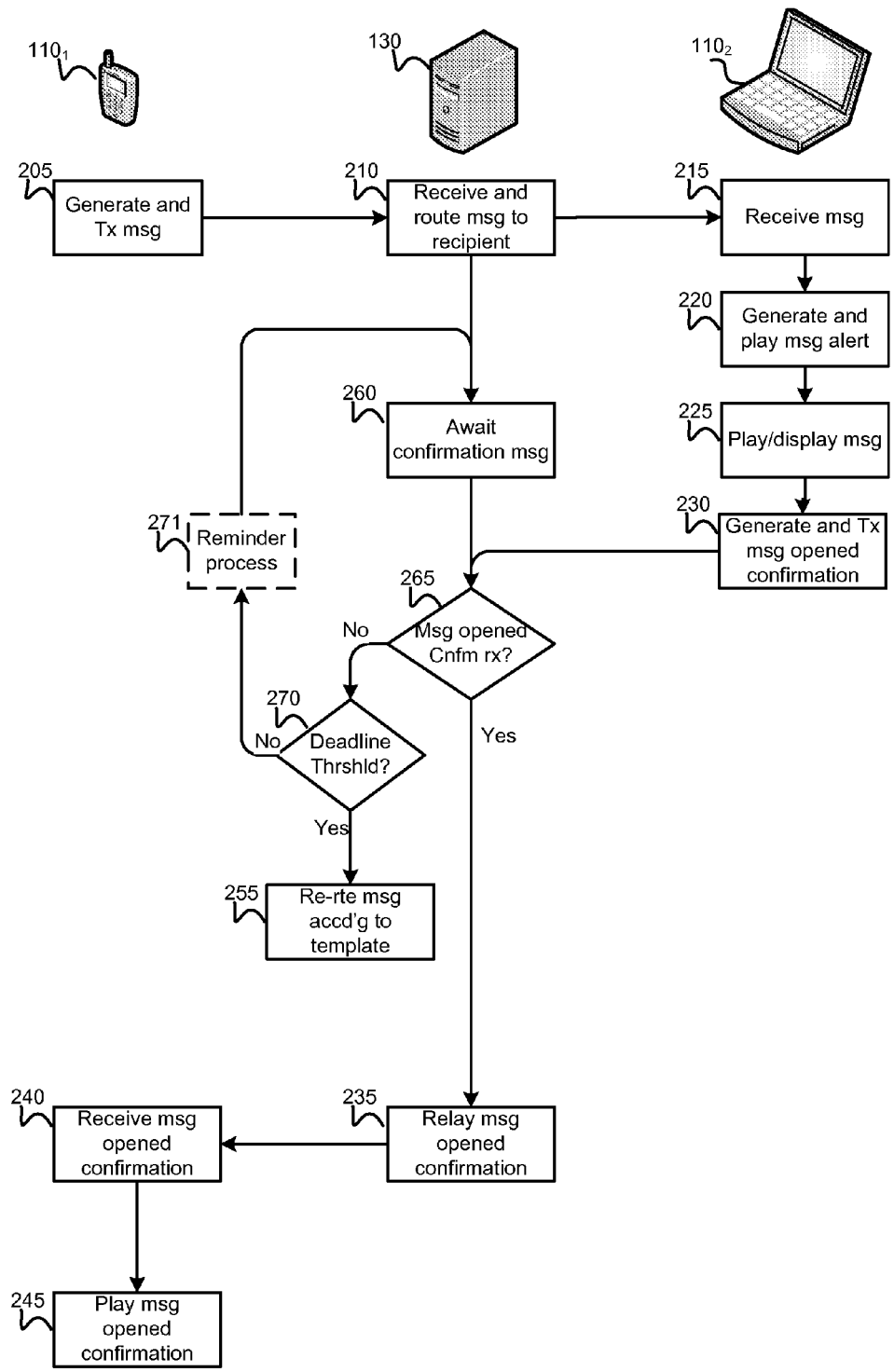
FIG. 4 is a process flow diagram of an embodiment method for re-routing a message when a sent message has not been read within a pre-determined time before a deadline.

FIG. 4 is a process flow of an embodiment method for re-routing a message if a response is not received within some deadline (automatic or manually imposed). Referring to FIG. 4, the mediator 130 receives and routes the message to the intended first recipient, step 210. After routing the message, the mediator 130 awaits the message opened confirmation so as to relay it on to the originating communication device $110_1$, step 260. The mediator 130 determines if the message opened confirmation is received, decision 265. If the message opened confirmation is received (i.e., decision 265=Yes), then the message opened confirmation may be relayed onto the originating communication device $110_1$ as described above with reference to FIGS. 2 and 3, steps 235-245. As mentioned above with reference to FIG. 3 and described in more detail below with reference to FIGS. 20-24, the mediator 130 may implement steps to monitor asynchronous message status to avoid duplicate responses to the asynchronous message. When the message opened confirmation is received for relay by the mediator 130, the mediator 130 may determine if the message opened confirmation is for an asynchronous message having multiple recipients.

If the message opened confirmation is not received (i.e., decision 265=No), the mediator 130 determines if the deadline has elapsed, decision 270. If the deadline has not elapsed (i.e., decision 270=No), the mediator 130 may continue to await the message opened confirmation, step 260. However, if the deadline has elapsed (i.e., decision 270=Yes), the message may be re-routed in accordance with the routing template, step 255. One of skill in the art would appreciate that the mediator 130 may impose a deadline of shorter duration than that imposed by the sender to re-route the message. By doing so the mediator 130 may ensure that the re-routed recipient receives the message with sufficient time to act before the sender's imposed or automatically imposed deadline expires. In addition, as mentioned above with reference to FIG. 3 and described in more detail below with reference to FIGS. 20-24, the mediator 130 may implement steps to monitor asynchronous message status to avoid duplicate responses to the asynchronous message. When the asynchronous message is routed by the mediator 130, the mediator 130 may establish a monitored message table data entry which maintains a listing of all recipients (original and re-routed) of the asynchronous message.

In an alternative embodiment, a reminder may be sent to the first recipient regarding the received asynchronous message. In such an alternative embodiment, a reminder may be generated by the mediator 130 to remind the first recipient that the received message must be opened (and acted upon) prior to the expiration of the deadline. In the alternative embodiment, if the deadline has not elapsed (i.e., decision 270=No), the mediator 130 may proceed to perform an optional reminder process 271.

Figure 5:
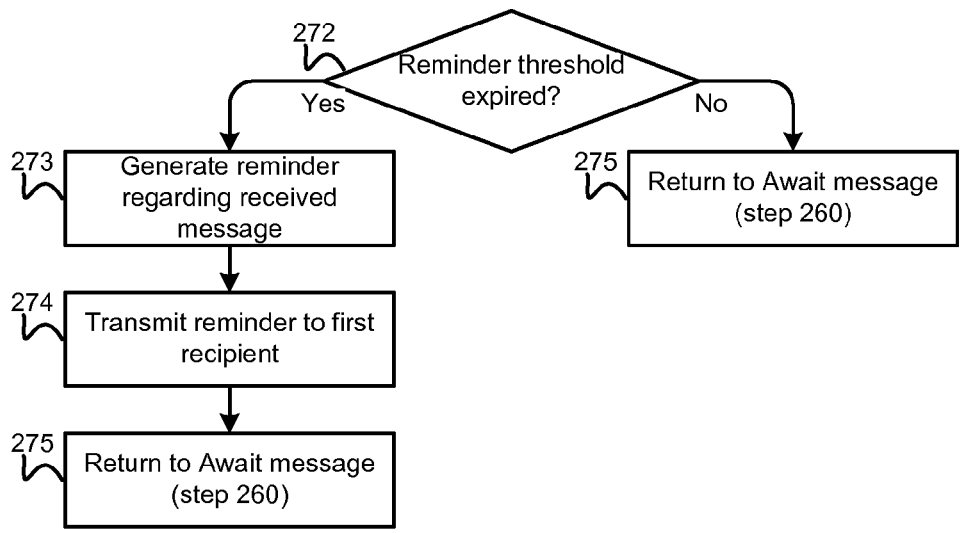
FIG. 5 is a process flow diagram of an embodiment method for sending a reminder to a first recipient prior to the expiration of a deadline.

FIG. 5 is a process flow diagram of an embodiment method (e.g., step 271) for sending a reminder to a first recipient prior to the expiration of a deadline. In this embodiment, if the deadline has not elapsed (i.e., decision 270=No), the mediator 130 may determine if a reminder threshold has expired, decision 272. The reminder threshold may be some period of time shorter than the deadline checked in decision 270 so that a reminder may be sent with sufficient time to remind the first recipient that the asynchronous message can be opened and acted upon prior to the expiration of the deadline. If the reminder threshold has not expired (i.e., decision 272=No), the mediator 130 may return to step 260 to await the message opened confirmation, step 275. However, if the reminder threshold has expired (i.e., decision 272=Yes), the mediator 130 may generate a reminder regarding the received asynchronous message, step 273. Once generated, the mediator 130 may transmit the reminder message to the first recipient, step 274. After transmission, the mediator 130 may return to step 260 to await the message opened confirmation, step 275.

In another embodiment, a secondary reminder may be sent to a second recipient. In some instances, a first recipient may not be checking their communication device 110 for received asynchronous messages. For example, an intended recipient of an asynchronous message may be checking their communication device 110. By sending a secondary reminder to a second recipient that may be in close physical proximity to the first intended recipient, the second recipient can physically remind the first recipient of the received message. As an example, the second recipient may be the first recipient's assistant, supervisor or colleague. Each of the possible second recipients may be assigned to the same role as the first recipient.

Figure 6:
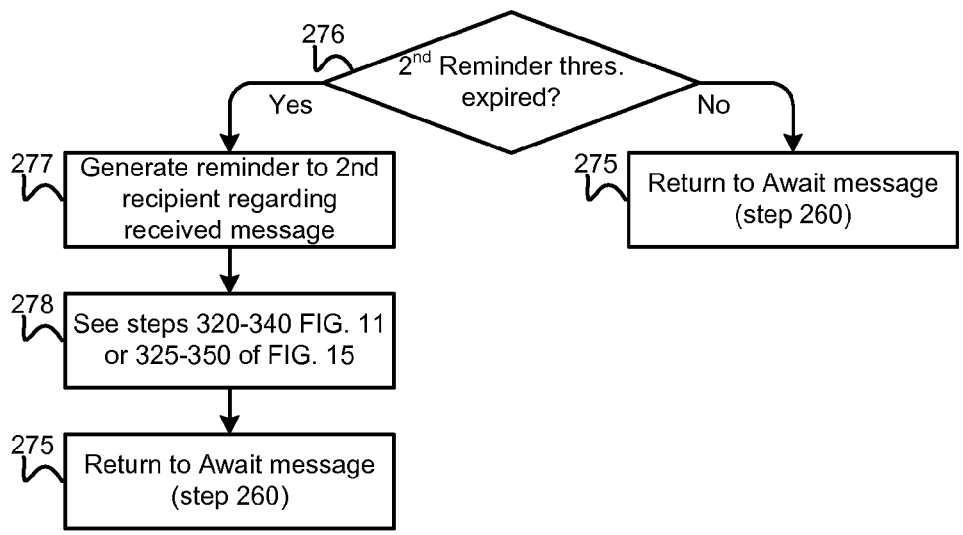
FIG. 6 is a process flow diagram of an embodiment method for sending a secondary reminder to a second recipient prior to the expiration of a deadline.

FIG. 6 is a process flow diagram of a method for sending a secondary reminder to a second recipient to physically remind the first recipient to respond to the message prior to the expiration of a deadline. The process illustrated in FIG. 6 may be implemented in place of or in conjunction with the reminder process illustrated in FIG. 5. If implemented in place of the process illustrated in FIG. 5, if the deadline has not elapsed (i.e., decision 270=No), the mediator 130 may determine if a secondary reminder threshold has expired, decision 276. If the secondary reminder threshold has not expired (i.e., decision 276=No), the mediator 130 may return to step 260 and await the message opened confirmation message, step 275. However, if the secondary reminder threshold has expired (i.e., decision 276=Yes), the mediator 130 may generate a secondary reminder regarding the asynchronous message sent to the first recipient, step 277. The secondary reminder may, for example, inform the secondary reminder recipient that the first recipient has received an asynchronous message that requires attention and request the second recipient to please physically remind/inform the first recipient of the asynchronous message. Once generated, the mediator 130 may select a secondary reminder recipient in a manner similar to the re-routing process (step 255) (as described in more detail with reference to steps 320-345 of FIG. 13 and steps 325-350 of FIG. 19) and transmit the secondary reminder to the secondary reminder recipient, step 278. Once the secondary reminder is sent, the mediator 130 may return to step 260 to await the message opened confirmation, step 275. The re-routing steps described below with reference to FIGS. 13 and 17 select the next highest priority actor for a specific role that is available as the second recipient. The secondary reminder recipient selection process may select the second recipient in reverse priority order (i.e., selecting the lowest priority actor listed in the re-routing template first) so that secondary reminders are sent to a recipient's assistant before a recipient's supervisor.

Figure 7:
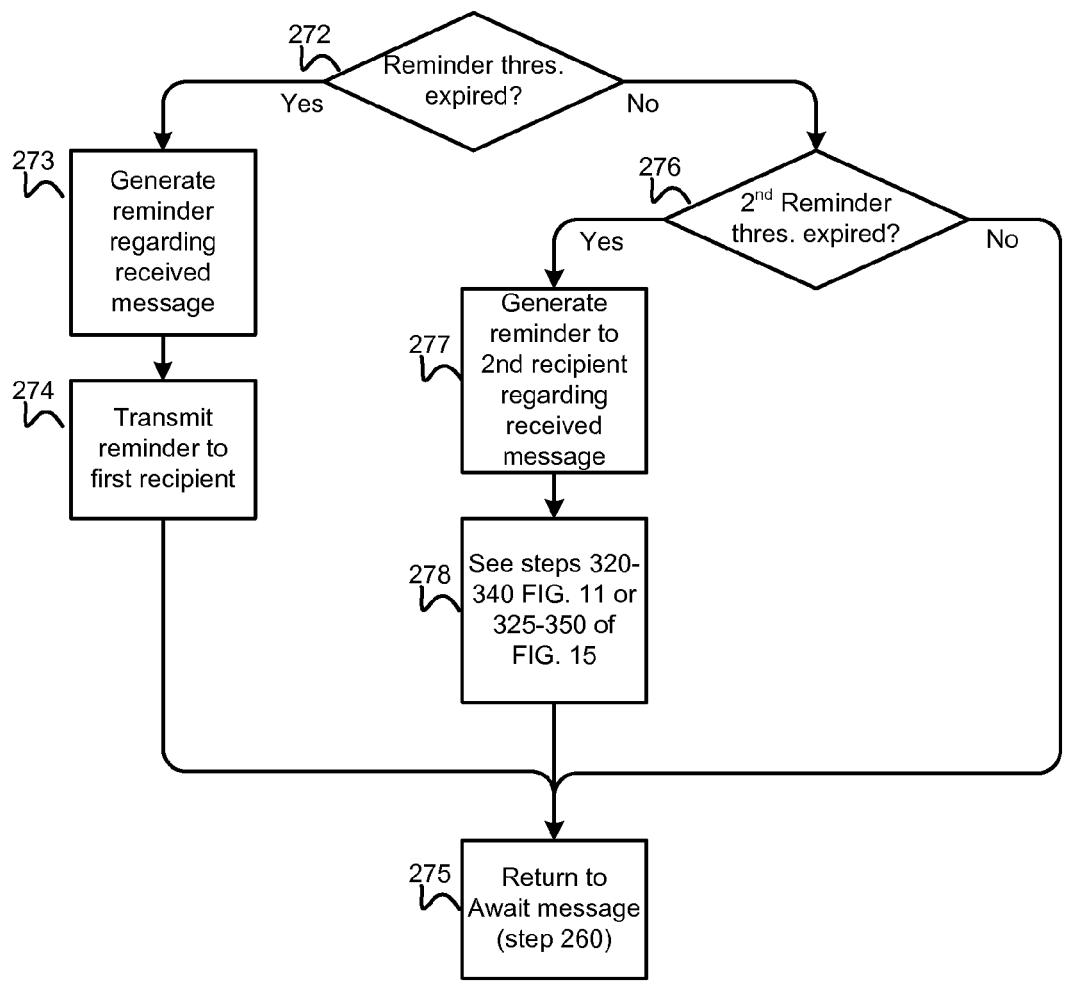
FIG. 7 is a process flow diagram of an alternative embodiment method which provides a first reminder in conjunction with a secondary reminder.

FIG. 7 is a process flow diagram of an alternative embodiment method which sends a secondary reminder to a second recipient to physically remind the first recipient to respond to the message prior to the expiration of a deadline (i.e., the process flow of FIG. 6) in conjunction with sending a reminder to the first recipient prior to the expiration of a deadline (i.e., the process flow of FIG. 5). In the process flow shown in FIG. 7, the first reminder threshold is contemplated to be of a longer duration than the secondary reminder threshold. In this manner, the secondary reminder recipient may be asked to physically remind/inform the first recipient about the received asynchronous message before sending the first recipient a subsequent (final) reminder that a response to the received asynchronous message is requested/required. In some situations, the secondary reminder recipient may be able to respond to the message on behalf of the first recipient, such as when the secondary reminder recipient can determine the information or consult with the first recipient. In any case, in order to be effective both the first and secondary reminder thresholds may be shorter in duration than the deadline threshold so that the reminders can be sent with sufficient time for either the first or second recipients to receive the reminders prior to the expiration of the deadline.

Referring to FIG. 7, if the deadline has not elapsed (i.e., decision 270=No), the mediator 130 may determine if the first reminder threshold has expired, decision 272. If the first reminder threshold has expired (i.e., decision 272=Yes), the mediator 130 may complete steps 273-275 in the same manner as described above with reference to FIG. 5. However, if the first reminder has not expired (i.e., decision 272=No), the mediator 130 may determine if the secondary reminder threshold has expired, decision 276. Since the secondary reminder threshold is of a shorter duration than the first reminder, it is possible that the secondary reminder threshold will have expired even if the first reminder threshold has not yet expired. If the secondary reminder threshold has expired (i.e., decision 276=Yes), the mediator 130 may complete steps 277, 278 and 275 in the same manner as described above with reference to FIG. 6. However, if the secondary reminder threshold has not expired (i.e., decision 276=No), the mediator 130 may return to step 260 to await the message opened confirmation, step 275.

Figure 8:
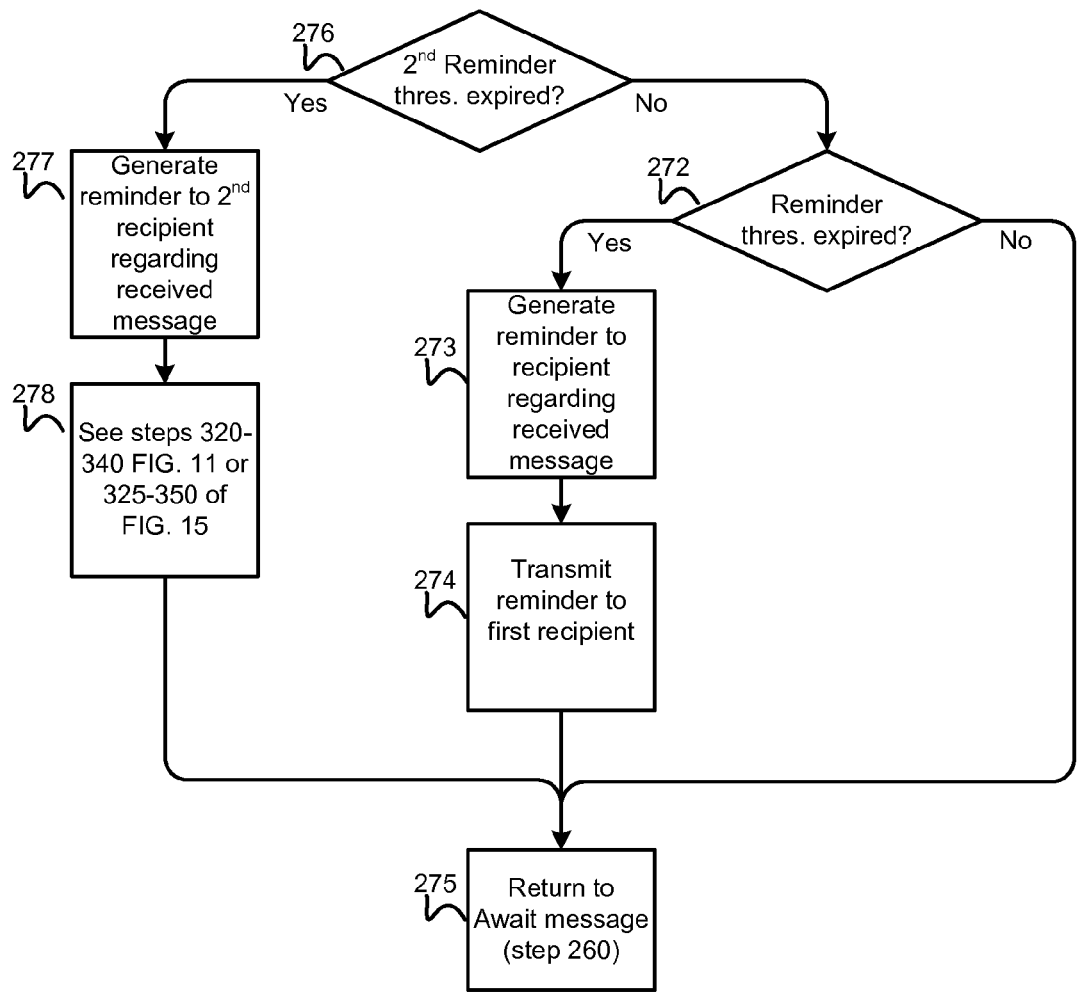
FIG. 8 is a process flow diagram of an alternative embodiment method which provides a first reminder in conjunction with a secondary reminder.

Alternatively, an AMC system 100 administrator may wish to implement the secondary reminder process and second recipient as a last (final) resort to remind/inform the first recipient of the received asynchronous message. Accordingly, the secondary reminder threshold may be of a longer duration than the first reminder threshold. In this manner, the first reminder may be sent to the first recipient before the secondary reminder is sent to the second recipient. FIG. 8 is a process flow diagram of an alternative embodiment method which performs the method for sending a reminder to a first recipient before the expiration of a deadline (i.e., the process flow of FIG. 5) prior to sending a secondary reminder to a second recipient requesting that person to physically remind the first recipient to respond to the message (i.e., the process flow of FIG. 6). Referring to FIG. 8, because the duration of the secondary reminder threshold is longer in this embodiment the secondary reminder threshold is checked first for expiration, decision 276. If the secondary reminder threshold has expired (i.e., decision 276=Yes), the mediator 130 may complete steps 277, 278 and 275 in the same manner as described above with reference to FIG. 6. However, if the secondary reminder threshold has not expired (i.e., decision 276=No), the mediator 130 continues to check if the first reminder threshold has expired, decision 272. The mediator 130 then proceeds to perform the steps 273-275 in the same manner as described above with reference to FIG. 5. In an embodiment, this process may be extended so that more than two reminders are sent before the process is escalated, in which case threshold timers associated with each layer of reminder messages may be adjusted to that such reminders are sent before the expiration of the message deadline.

It may also be the situation that prior to receiving the message opened confirmation, the sender's communication device $110_1$ becomes unavailable. To avoid duplication of efforts the message open confirmation may be re-routed to the actor fulfilling the role of the unavailable sender. For example, as the last act of a shift a doctor may send a request for lab results. The doctor may realize that he/she will not be available when the test results are expected to be returned. Nevertheless, the doctor may desire to inform the doctor taking over his/her shift that the test results were requested. To enable this, the message opened confirmation may be re-routed to the actor fulfilling the doctor's role to receive the message opened confirmation.

Figure 9:
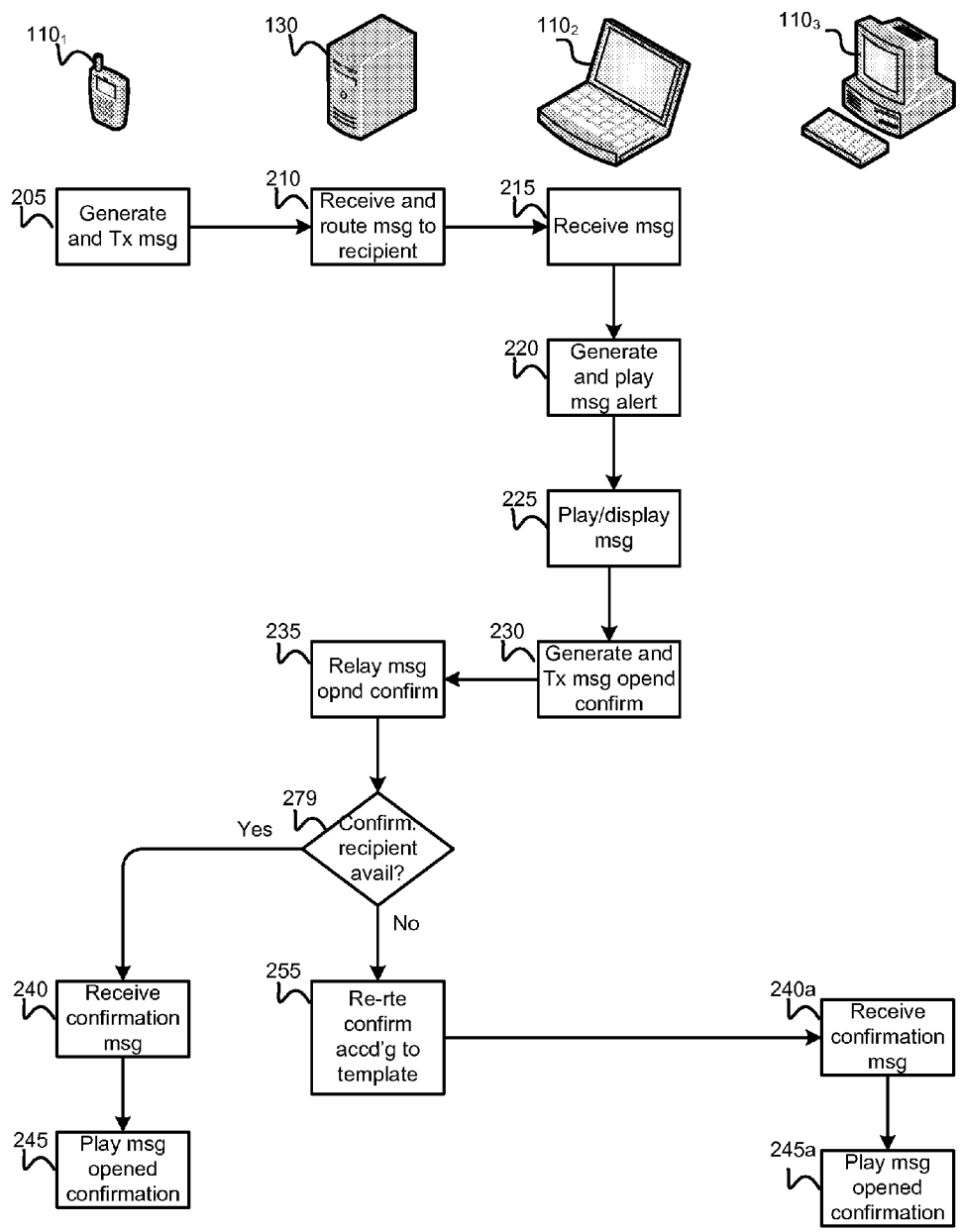
FIG. 9 is a process flow diagram of an embodiment method for re-routing a read confirmation message when the originating device is no longer available.

FIG. 9 is a process flow diagram of an embodiment method for re-routing a message opened confirmation when the originating device is no longer available. When the first recipient opens a sent message, the message opened confirmation is generated and sent back to the sender, step 205-235. Upon receiving the message opened confirmation, the mediator 130 may determine if the sender's communication device $110_1$ is available, decision 279. If the sender's communication device $110_1$ is available (i.e., decision 279=Yes), the message opened confirmation is relayed to the sender's communication device $110_1$ where it is played or displayed as described above with reference to FIGS. 2-4 (step 235-245). However, if the sender's communication device $110_1$ is not available (i.e., decision 279=No), the message opened confirmation may be re-routed in accordance with a routing template, step 255. Using the routing template discussed briefly above and in more detail below with reference to FIGS. 14a-14c, the message opened confirmation may be re-routed to an actor fulfilling a role appropriate to receive the message opened confirmation, steps 240a and 245a.

Figure 10:
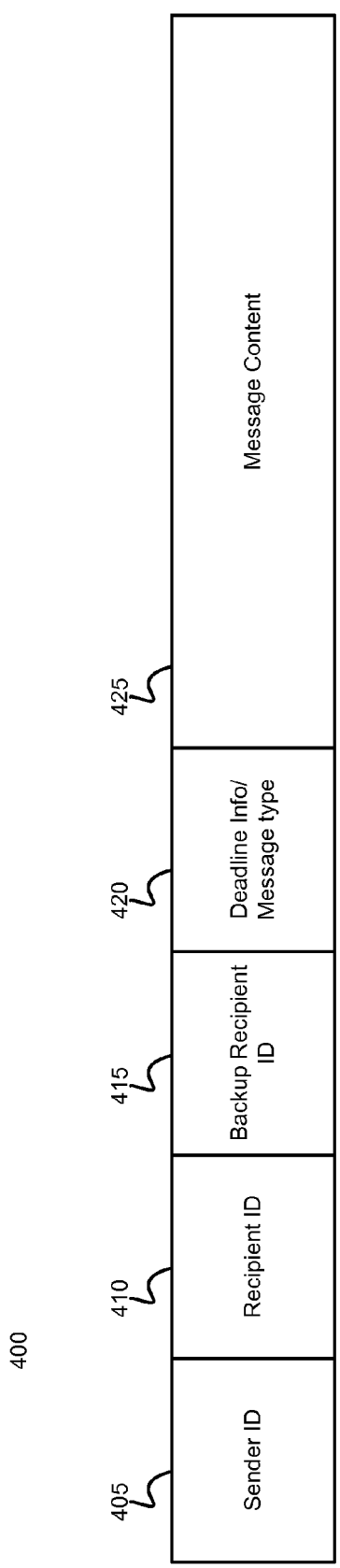
FIG. 10 is an example of a message structure for use in an embodiment method for insuring delivery and action upon a sent message.

Each message may contain routing information as well as deadline information which allow the mediator 130 to properly route and re-route messages in a timely manner. FIG. 10 is an example of a message structure for use in an embodiment method for insuring delivery and action upon a sent message. The message may include the originating sender's ID 405, the intended recipient's ID 410, the backup recipient's ID 415, the deadline information or message type 420, and the message content payload 425. In an embodiment, the originating sender's ID 405 may be the originating sender's IP address, phone number, email address, or mobile device identifier (MID). Similarly, the recipient's ID 410 and backup recipient ID 415 may also be either the recipient's or the backup recipient's SIP address, phone number, email address, or mobile device identifier (MID). The message content payload 425 may be expressed in a format specified for the type of message, for example, in an XML format. The message content payload intended for a recipient may be protected using a "security" key that is assigned to the role being fulfilled by the recipient actor. Encrypting the message payload will typically be accomplished when the message includes patient personal information. In an example, the message content is in the XML format and XML security standard is used to protect the message content.

The mediator 130 may route the message 400 to the intended recipient using the recipient ID 410 information. Message routing processes defined for the particular message type may be implemented to deliver the message to the recipient. Likewise, the mediator 130 may route message opened confirmations (which could imply that the recipient has taken ownership of the appropriate action required by the message) to the originating sender using the sender ID 405 information. As discussed above with reference to FIG. 4, if a message opened confirmation is not received and relayed on to the originating communication device $110_1$ within some threshold of time, the mediator 130 may attempt to re-route the message 400. By using the deadline information 420 contained within the message structure 400, the mediator 130 may determine the appropriate time to re-route the message 400. The mediator 130 may re-route the message 400 to a specified backup recipient using the backup recipient ID 415 information.

Alternatively, if the message type is identified in sub-field 420 (as opposed to explicit deadline information) the mediator 130 may retrieve a previously stored message flow routing rule from either local mediator memory or the mediator database 135 to impose a deadline for the message type. In this manner, the mediator 130 may impose a deadline on messages 400 even if the sender failed to enter a deadline in sub-field 420. Thus, the deadline would depend on the message type identified in sub-field 420.

Multiple individuals may be identified and entered in each of sub-fields 405, 410, and 415. Regardless of the number of identified recipients (or backup recipients), the mediator 130 may re-route the message 400 if a message opened confirmation is not relayed on to the sender within some threshold of time.

Figure 11:
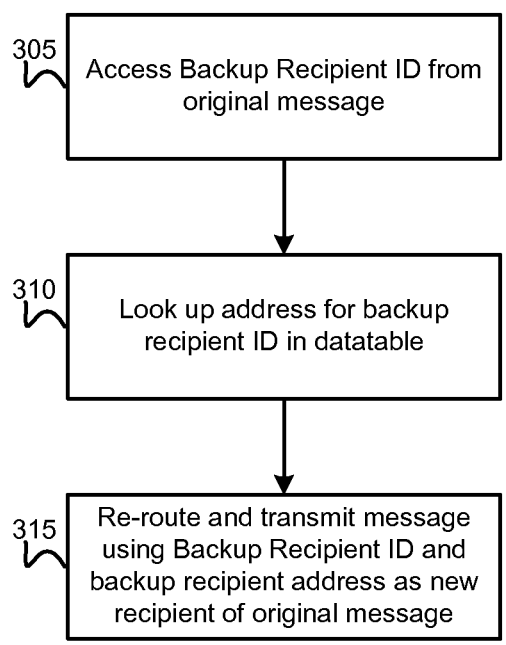
FIG. 11 is a process flow diagram of an embodiment method for re-routing a sent message to an alternative recipient.

FIG. 11 is a process flow diagram of an embodiment method for re-routing a sent message to an alternative recipient (see step 255 in FIGS. 2-9). In instances where a message 400 having the structure shown in FIG. 10 is employed, upon determining that the message 400 should be re-routed the mediator 130 may access the backup recipient ID information 415 from the original message 400, step 305. If the backup recipient's ID does not include an explicit address (e.g., SIP address, phone number, email address, or MID), the mediator 130 may lookup the address of the backup recipient from a database or re-routing template stored in local mediator 130 memory, step 310. Using the backup recipient's address, the original message 400 may be re-routed and transmitted to the backup recipient, step 315.

Figure 12:
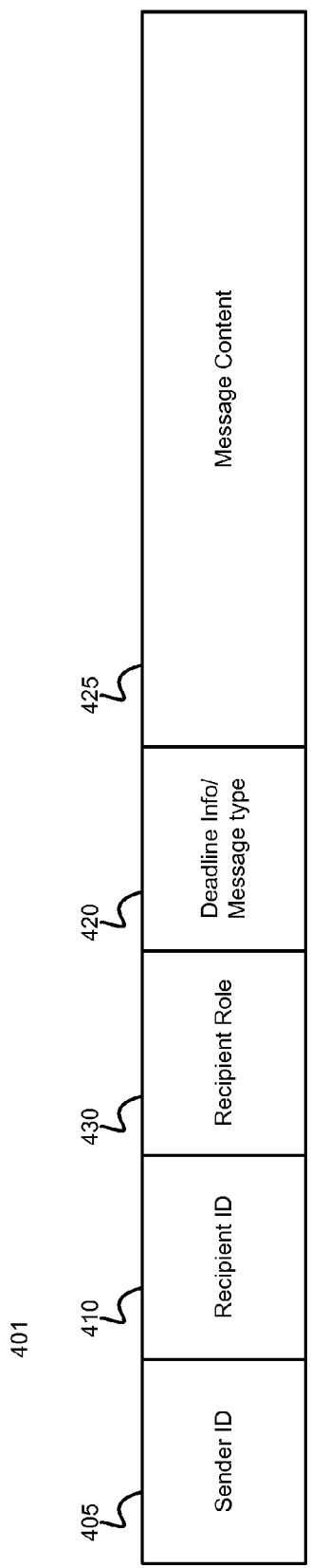
FIG. 12 is an example of an alternative message structure for use in an embodiment method for insuring delivery to an alternative recipient based upon the role performed by the intended and alternative recipients.

FIG. 12 is an example alternative message structure for use in an embodiment method for insuring delivery to an alternative recipient based upon the role performed by the intended and alternative recipient. As with message 400 shown in FIG. 10, message 401 depicted in FIG. 12 contains the sender's ID 405, the recipient ID 410, deadline info/message type 420 and the message content payload 425. However, the message also contains a data field for the recipient's role 430. In routing the message 401, the mediator 130 may also consider the role of the actor assigned to the first recipient communication devices $110_2$.

In sending a message to a specific actor, the sender may also identify the role performed by the recipient 430. By identifying the role of the intended recipient within the message header the mediator 130 may be able to re-route the message to another actor performing the same role as the intended recipient.

Figure 13:
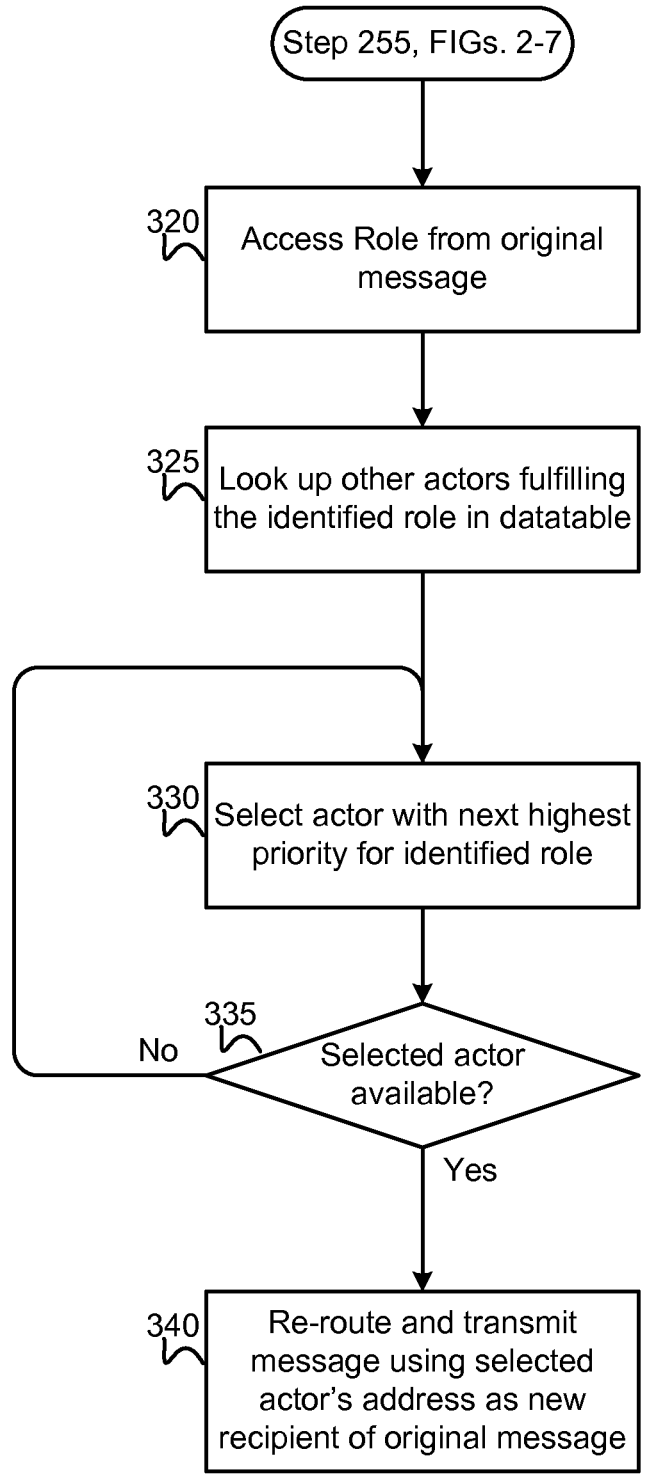
FIG. 13 is a process flow is a process flow diagram of an embodiment method for re-routing a message to an alternative recipient based upon a role performed by the intended recipient and the alternative recipient.

FIG. 13 is a process flow diagram of an embodiment method in which an asynchronous message is re-routed to a backup recipient according to the role that the intended recipient performed. If the mediator 130 determines that the message (or message opened confirmation) must be re-routed (see step 255 in FIGS. 2-9), then the mediator 130 processor may access the role of the intended recipient from the original message role sub-field 430, step 320. Alternatively, the mediator 130 processor can determine the role of the recipient by using the name or ID of the intended recipient from the message recipient ID sub-field 410 as a look up value in a personnel directory or routing template stored in local memory of the mediator 130 or in a mediator database 135. Knowing the intended recipient's role, the mediator 130 processor may lookup other actors fulfilling the same role from a routing template stored in local memory of the mediator 130 or in a mediator database 135, step 325. Actors may be listed in priority order or have a priority value associated with their data records that the mediator 130 may use to select a particular backup recipient. The mediator 130 processor may determine the actor with the next highest priority of the identified role listed within the routing template, step 330. The priority order of actors or the priority values assigned to actors may be irrespective for each actor's availability. Once the actor with the next highest priority of the identified role is selected, the mediator 130 processor may determine whether the selected actor is available, determination 325. The mediator 130 processor may determine an actor's availability by looking up the selected actor's status in a dynamic availability table (see FIG. 14c). If the selected actor is available (i.e., determination 335=Yes), the message may be re-routed and transmitted to the selected actor's communication device, step 340. The message may be re-routed using address information contained within the routing template (see FIGS. 14*a* and 14*b*). If upon reviewing the dynamic status template (see FIG. 14*c*) the mediator 130 processor determines that the selected actor is not available (i.e., determination 335=No), the mediator 130 processor may access the routing template again to select the actor with the next highest priority level for the identified role, step 330.

FIG. 14*a* illustrates an example routing template that identifies the actors performing a particular role. In the illustrated example, only the portion of the routing template that includes actors performing the role of treating patient number 1 are listed. As one of skill in the art will appreciate, this table may be expanded by listing all roles. As shown in this example routing template, four doctors have been assigned the role of treating patient 1. For example, these doctors may include the patient's primary care physician, a specialist, an attending physician as well as resident physicians or medical students assigned to the treatment of patient 1. Other healthcare professionals assigned to patient 1 may also include nurses (Nurse A to Nurse C) and Physician Assistants (PA A and PA B). For messages related to patient 1, any of theses actors may be relevant recipients for a message related to treating patient 1. In addition to listing the actors role (in this example selection treating patient 1), the routing table may include a priority value for each actor associated with the identified role, a primary address (e.g., an e-mail address as shown) for sending messages and a back up address (e.g., a telephone number for sending SMS messages as shown). Again, FIG. 14*a* illustrates just a portion of an example template in which roles are defined by a patient. In another implementation, for example, the routing template may specify that all messages for doctor A's patients get routed to Doctor B (this happens in delegation for example). In a further example, the routing template could specify that all calls to a particular ICU physician should be routed to the Medical Director if the particular physician is not available.

FIG. 14*b* illustrates another portion of the routing table for which the role is the actors' job type. In the instant example shown in FIG. 14*b*, the portion of the routing table including the specific job type "nurse." The priority level of each nurse listed may be in descending order, such as from supervisor (Nurse A) to rank and file nurses (Nurses B-Nurse E). Thus, if the original message identifies the role in the message role sub-field 430 as "nurse" (as opposed to "patient 1" shown in FIG. 14*a*), the portion of the routing template shown in FIG. 14*b* may be retrieved in step 325 of FIG. 13 as opposed to the portion of the routing template shown in FIG. 14*a*. Regardless, the same dynamic status template may be used to determine the current status of each actor.

The dynamic status template depicted in FIG. 14*c* may be updated in real time through any of a variety of methods. For example, each time an actor logs into the AMC system 100 via any communication device 110$_n$, the actor's status may change from "Out" to "In." Alternatively, the dynamic status template may be set to change in accordance with a work schedule which is manually updated. In another embodiment, the dynamic status template may be linked to (or potential implemented as part of) an enterprise calendar and appointment system, such as a Microsoft Outlook® profile for example. In yet another embodiment, an actor's current status may change as the actor's communication device comes into and goes out of range of the communication network 120. By dynamically changing the availability status of the various actors, the message may be properly re-routed to only actor's who are currently available to receive message. In this manner, some communication breakdowns may be removed from the system.

To illustrate use of the routing templates shown in FIGS. 14*a* and 14*c*, a message regarding patient 1 might be sent to Doctor C as the first recipient. In formatting this message, the sender's communication device generates a message that identifies treating patient 1 (or team member treating patient 1) as the role that Doctor C is performing with respect to the sent message. If Doctor C is currently "Out" (see FIG. 14*c*) Doctor C will not respond to the sent message and therefore a message opened confirmation will not be returned to the mediator 130. When either the threshold time prior to the deadline expressed in the message deadline information sub-field 420 or a threshold time prior to the deadline imposed by the mediator 130 due to the message type 420 has elapsed, the mediator 130 processor may access the first recipient's role from the original message 401 (see step 320 in FIG. 13). After retrieving the appropriate role from the original message, which is patient 1 team members in the instant example, the mediator 130 processor may access the routing template for the role "patient 1" to look up other actors fulfilling the identified role (see step 325 in FIG. 13). The mediator 130 processor may select the actor with the next highest priority for the identified role (see step 330 in FIG. 13). In the instant example Doctor A has the highest priority (priority=1). The mediator 130 processor then determines whether Doctor A is available by looking up Doctor A's current status in a dynamic status template such as shown in FIG. 14*c*. The dynamic status template shown in FIG. 14*c* shows that Doctor A is currently "Out" (i.e., not available), so the mediator 130 processor accesses the routing template for patient 1 team members again to select the actor with the next highest priority (see step 330 in FIG. 13). The routing template in FIG. 14*a* for patient 1 team members shows that Doctor B has the next highest priority (priority=2). The mediator 130 processor then determines whether Doctor B is available by looking up Doctor B's current status in the dynamic status template shown in FIG. 14*c*. The dynamic status template shows that Doctor B is also currently "Out" (i.e., not available). Therefore, the mediator 130 processor accesses the routing template for patient 1 team members again to select the actor with the next highest priority (step 330). This process may continue until the selected actor is determined to be available. In the instant example, the selected actor with the next highest priority who is also available is Doctor D. Therefore, in this example the mediator 130 processor retrieves the addresses associated with Doctor D from the routing template and relays the original message 401 to Doctor D (see step 340 in FIG. 13).

One of skill in the art would appreciate that FIGS. 14*a*-14*c* are representative example data structures and that the various embodiments may be implemented using a variety of different data structures. For example, multiple cross-indexed data tables may be used so that actor information is listed in only one table (e.g., a single table listing for each actor's contact information, role, responsibility, organizational position, etc.). Routing template may further specify the role which the listed actors perform. For example, in addition to having a routing template for "patient 1 team members," there may be an additional routing template created for "patient 1 nurses," "patient 1 PAs." Likewise, there may be routing templates which specifies "emergency room nurses," "pediatric nurses," "oncology nurses," etc.

Figure 19:
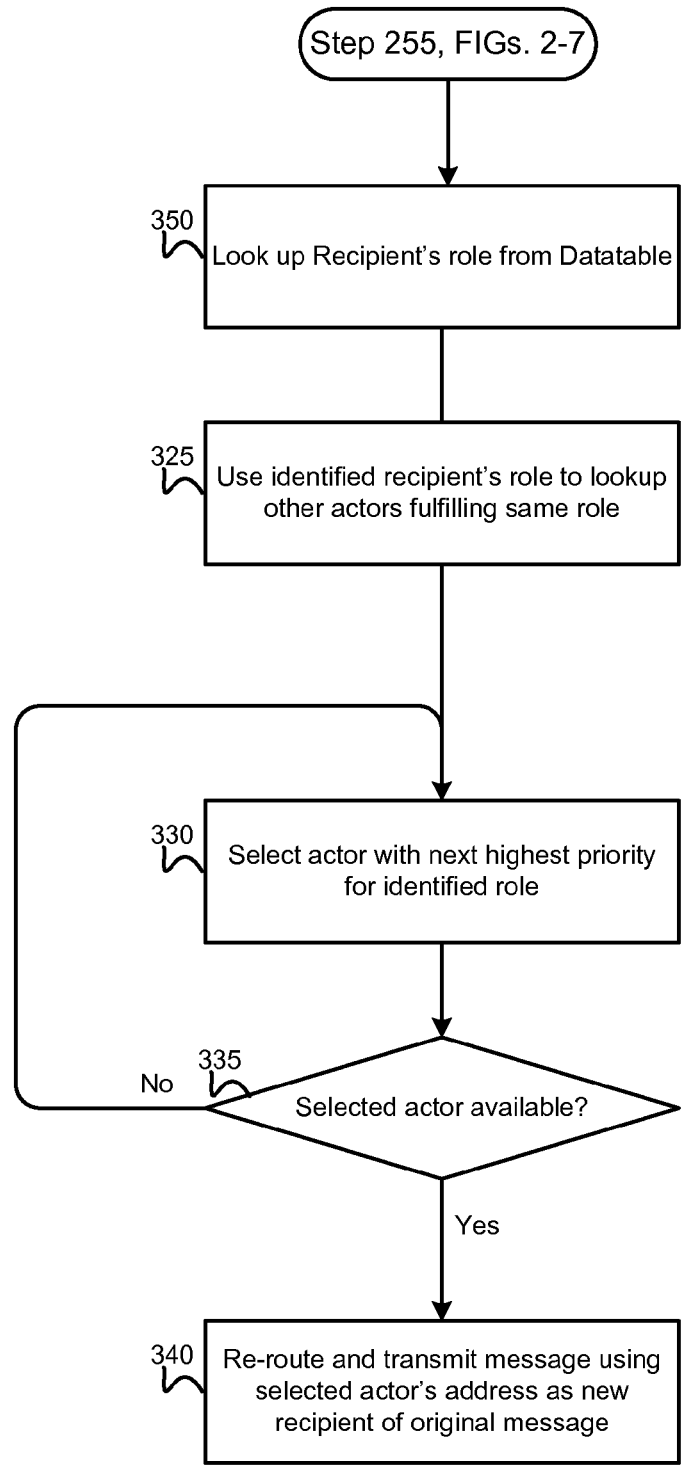
FIG. 19 is a process flow diagram of an embodiment method for re-routing a message to an alternative recipient based upon a role performed by the intended recipient and alternative recipient.

In an alternative embodiment, the message structure may not contain a sub-field for the recipient's role. For example, FIG. 15 illustrates an example message structure which includes the originating sender's ID 405, the intended recipient's ID 410, deadline information or message type 420, and the message content payload 425. Absent from this message structure 402 is an indication of the recipient's role or a backup recipient. In order to properly re-route such messages in an AMC system 100, the mediator 130 processor may implement a method such as illustrated in the process flow shown in FIG. 19. Referring to FIG. 19, if the mediator 130 determines that the message (or message opened confirmation) must be re-routed (see step 255 in FIGS. 2-9), the mediator 130 processor may search the re-routing templates for the intended recipient's ID and lookup the intended recipient ID's associated role, step 350. Once the role is determined, the mediator 130 processor may re-route the message in the same manner as described above with reference to steps 325-345 in FIG. 13. The message structure 402 and the alternative embodiment method illustrated in the process flow of FIG. 19 may be implemented in environments in which each actor appears in a single routing template. In this manner, the role of the actor may be determined by searching a single routing template in which the actor is listed. For example, actors may be organized into teams and thus, a message can be re-routed to other team members. Alternatively, in instances where each actor may appear in multiple routing templates, the mediator 130 may attempt to obtain additional information from the message itself to determine the role of the intended recipient. For example, the mediator 130 may look to the message type, patient identifiers, roles of sender, a previous sender, or recipients of earlier messages in a message thread, and any combination of these or other parameters, to determine the role of the intended recipient. Such multi-factor determinations may use logic tables or artificial intelligence rules engines in order to effectively reroute the message to a unique endpoint (i.e., ultimate recipient).

FIG. 16 is an example message structure for use in another alternative embodiment. In this message structure 403 neither the sender's ID nor the recipient's ID is included. Instead only the roles of the both the sender and intended recipient are included in the message structure sub-fields 450 and 455, respectively. In order to properly route such message 403, the mediator 130 processor retrieves the routing templates (e.g., FIGS. 14a-14c) in the initial routing procedure. In instances where the sender specifies the intended recipient by role only, the mediator 130 processor may retrieve the appropriate routing template in accordance with the specified recipient role 455 and determine the appropriate recipient by implementing a method such as described above with reference to FIG. 13. Thus, the process of selecting a recipient for a message is performed for both initial routing and for re-route the message in the event a message opened confirmation is not returned within the deadline period. In the alternative embodiment using a message structure 403 as shown in FIG. 16, message senders may not be aware of or care who the recipient of the message is. Rather, the sender may only know the specific role which should receive and act/respond to the message 403.

Figure 17:
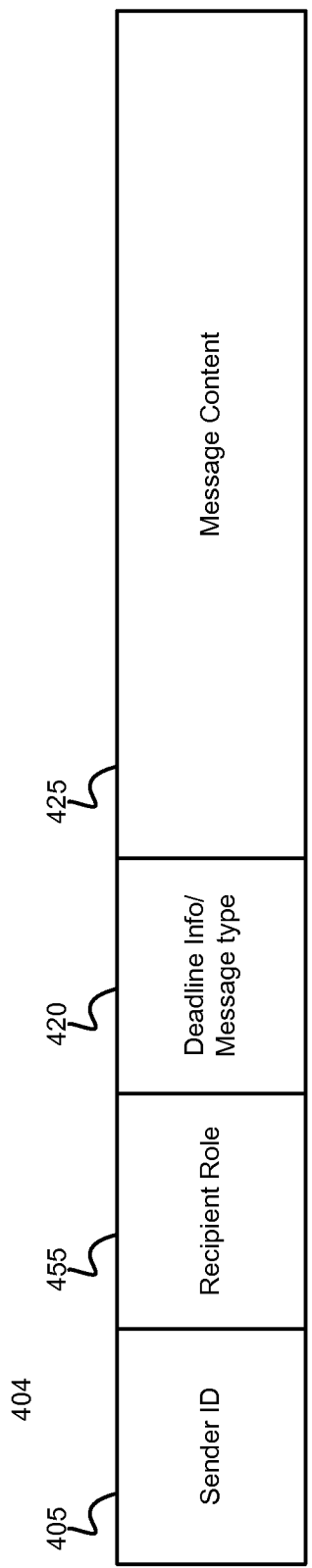
FIG. 17 is an example of a message structure for use in an embodiment method for insuring delivery of and action upon a sent message.

FIG. 17 is an example message structure for use in another alternative embodiment. In this message structure 404 only the sender's ID 405 and the recipient's role 455 is included. In many instances, a sender will not know the ID of a specific actor fulfilling an identified role. Consequently, the sender may only identify which role is qualified to receive and/or respond to the message. In order to properly route such message 404, the mediator 130 processor retrieves the routing templates (e.g., FIGS. 14a-14c) in the initial routing procedure. As with the data structure shown in FIG. 16, the mediator 130 processor may retrieve the appropriate routing template in accordance with the specified recipient role 455 and determine the appropriate recipient by implementing a method such as described above with reference to FIG. 13. In the alternative embodiment using a message structure 404 as shown in FIG. 16, message senders may not be aware of or care who the recipient of the message is. Rather, the sender may only know the specific role which should receive and act/respond to the message 404. Message structure 404 differs from the message structure 403 illustrated in FIG. 16 in that the sender's ID is identified in sub-field 405 as opposed to simply the sender's role being identified in sub-field 450 of message structure 403.

Figure 18:
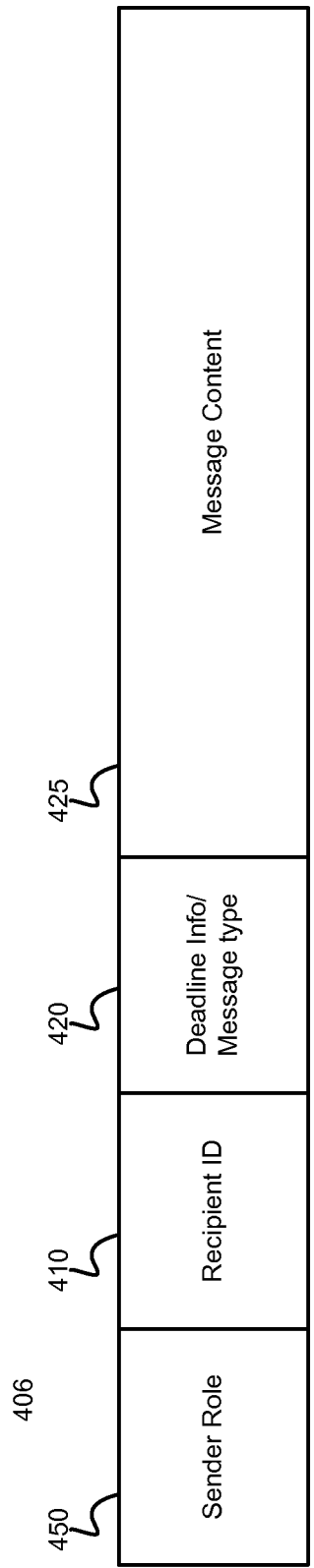
FIG. 18 is an example of a message structure for use in an embodiment method for insuring delivery of and action upon a sent message.

FIG. 18 is an example message structure for use in another alternative embodiment. In this message structure 406 only the sender role 450 and the recipient's ID 410 is identified in the message structure sub-fields. In some instances a sender may send a message from a shared communication device 110. For example, a desktop computer may be deployed at a nurse's station for all nurses, from which messages may be sent. Thus, the role of all senders may be known, but the specific sender ID may not be known. Messages may be sent by identifying specific recipient IDs. Any message opened confirmation would be routed in accordance with the routing templates to the same role that may be assigned to the communal communication device (e.g., nurse station computer).

One of skill in the art would appreciate that originating messages may be sent using any of the various embodiment message structures. Response message may be formulated using the same message structure as the originating message or any of the various embodiment message structures disclosed herein.

Additional features of the AMC system presented in FIG. 1 include mediated broadcast, real-time deadline notification, implementation of priority levels using deadlines, dynamic reminders, verbosity control and one-to-many communication. The mediated broadcast feature allows sending a message to multiple recipients (e.g., a one-to-many communication feature) and monitoring to whether the message was received, read and acknowledged. The one-to-many communication feature allows for one-to-many asynchronous communication. For example, a message initiated by $110_1$ can be broadcast to recipient communication devices $110_2$, $110_3$, ... $110_N$. The mediator 130 may monitor the receipt of message opened confirmations to confirm that the message is received, read and acknowledged by each of the recipient communication devices $110_2$, $110_3$ ... $110_N$. In one aspect, confirmation messages are sent back to the originating communication device $110_1$. In one aspect, the mediated broadcast feature includes simultaneous broadcast to the multiple recipients. In another aspect, the mediated broadcast feature includes non-simultaneous broadcast of the message.

The real-time deadline notification feature allows a status check of a message and modification of the deadline based on communication needs (e.g., message content). In one aspect, access to the status check feature is limited to predetermined actors, roles, recipients and/or combination thereof. In one aspect, authority to modify the deadline is limited to predetermined actors, roles, recipients and/or combination thereof. Using an example in the healthcare industry, a message may be sent to a nurse and a physician simultaneously. The nurse may be given access to check status sufficient to see if the physician has read the message. In an example, the nurse may resend the message to the physician if the status indicates that the physician has not read the message. The resent message may include an alert notification indicating the message priority level. In another example, the nurse may modify a deadline based on the need of the message content and resend the message to the physician with the modified deadline. These examples illustrate status checking, manual intervention and modification of a deadline.

The AMC system disclosed herein includes the feature of implementing priority levels using deadlines. The priority level of a message may be assigned based on the deadline(s) associated with the message. The deadline(s) in turn may depend on the criticality of the message content. In one example, the more critical the message content, the shorter the deadline by which the message needs to be conveyed to the recipient and the higher the priority level.

In an embodiment, a reminder may be sent to the recipient if a message is not read within a deadline. In one aspect, the reminders are sent to other actors fulfilling the role of the intended recipient or other roles entirely. For example, if a message is not read by any doctor in a routing-re-routing template within a threshold of time, a reminder message may be sent to nurses who can locate and remind the doctors that a message must be played or displayed. In one example, the roles are determined based on one or more of the following: message content, priority level, actor playing the role and/or combination thereof, etc. In one aspect, reminders may be added or modified as conditions change or if additional reminders or modification of reminders are necessary. In an example, a reminder is in the form of a deadline.

The verbosity control feature allows for message verbosity control to fine tune the types of messages received by a recipient. In one aspect, the parameters of the verbosity control are based on inputs such as a user's location, role, time, etc. The user in this example could include the sender and/or the recipient. In one aspect, one or more of the parameters of the verbosity control determines the allowable message length. It would be apparent to those skilled in the art that the above-mentioned features of the AMC system may be implemented individually or in combination with other features to achieve the concept of asynchronous mediated communication without affecting the spirit or scope of the present disclosure.

In one aspect, the message includes associated metadata for enabling one or more of the following features: role-based message routing, message redirection, mediated broadcast, real-time deadline modification, implementation of priority levels based on deadlines, dynamic reminders or verbosity control to achieve asynchronous mediated communication.

As multiple recipients receive an asynchronous communication message either originally or through the re-routing process, some confusion or duplication of effort in responding to the message could result. For example, in the healthcare industry, it is often the case that the particular individual responding to a message is not critical. However, it may be critical that someone respond to the message. Because the message may be originally routed and/or re-routed to multiple recipients, it is possible that multiple recipients might respond to the message concurrently without knowing that other recipients have already responded or are responding to the message. This duplication of effort is not only inefficient, but the duplicate responses may cause confusion, such as to which recipient should be contacted for follow-up or when multiple orders are issued. Accordingly, a method to monitor responses to a message to avoid duplicate responses to messages may improve efficiency and reduce confusion.

Figure 20:
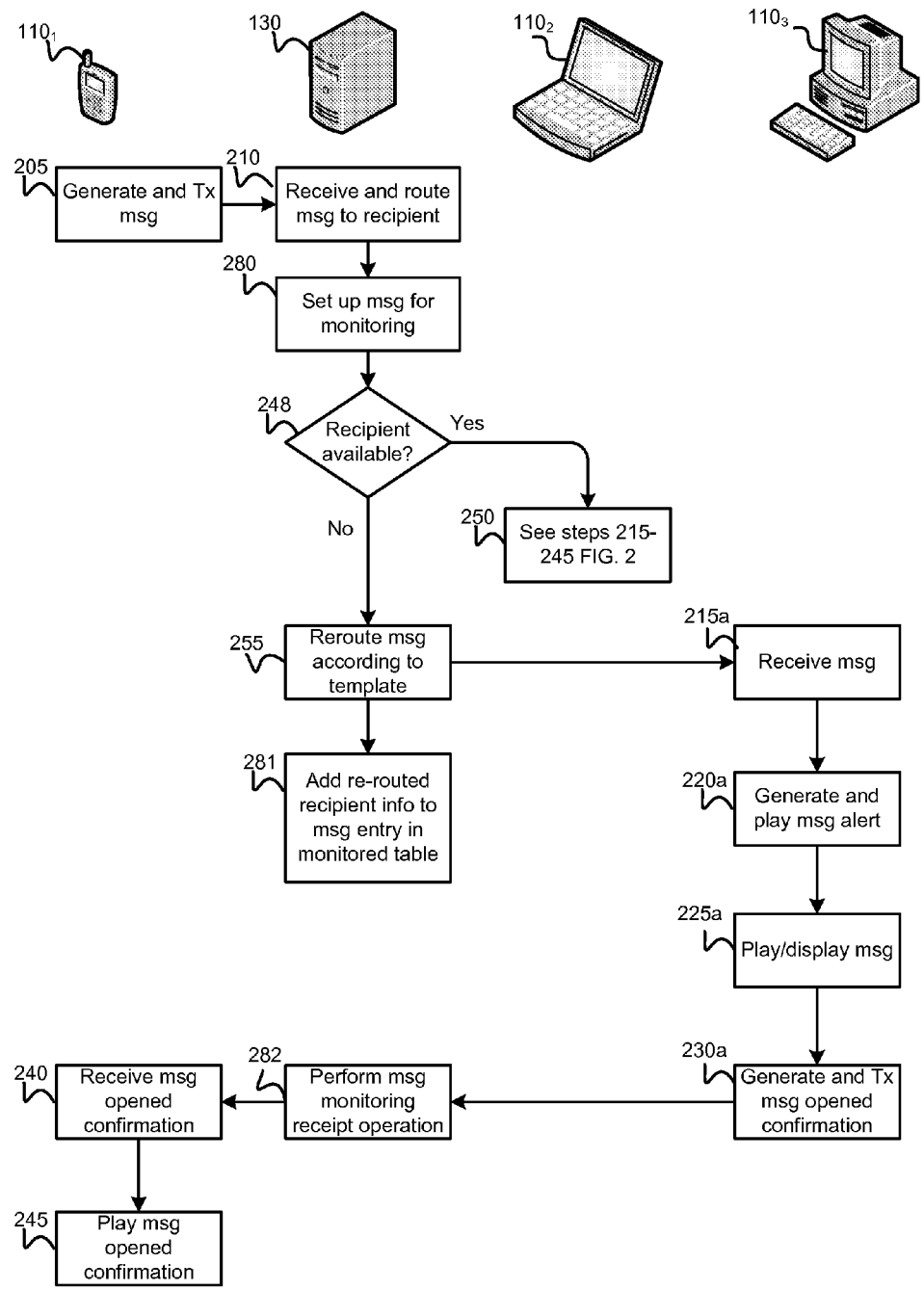
FIG. 20 is a process flow diagram of an embodiment method for re-routing a message when an intended recipient is unavailable in an asynchronous mediated communication network and monitoring the message status to avoid duplicate responses.
Figure 21:
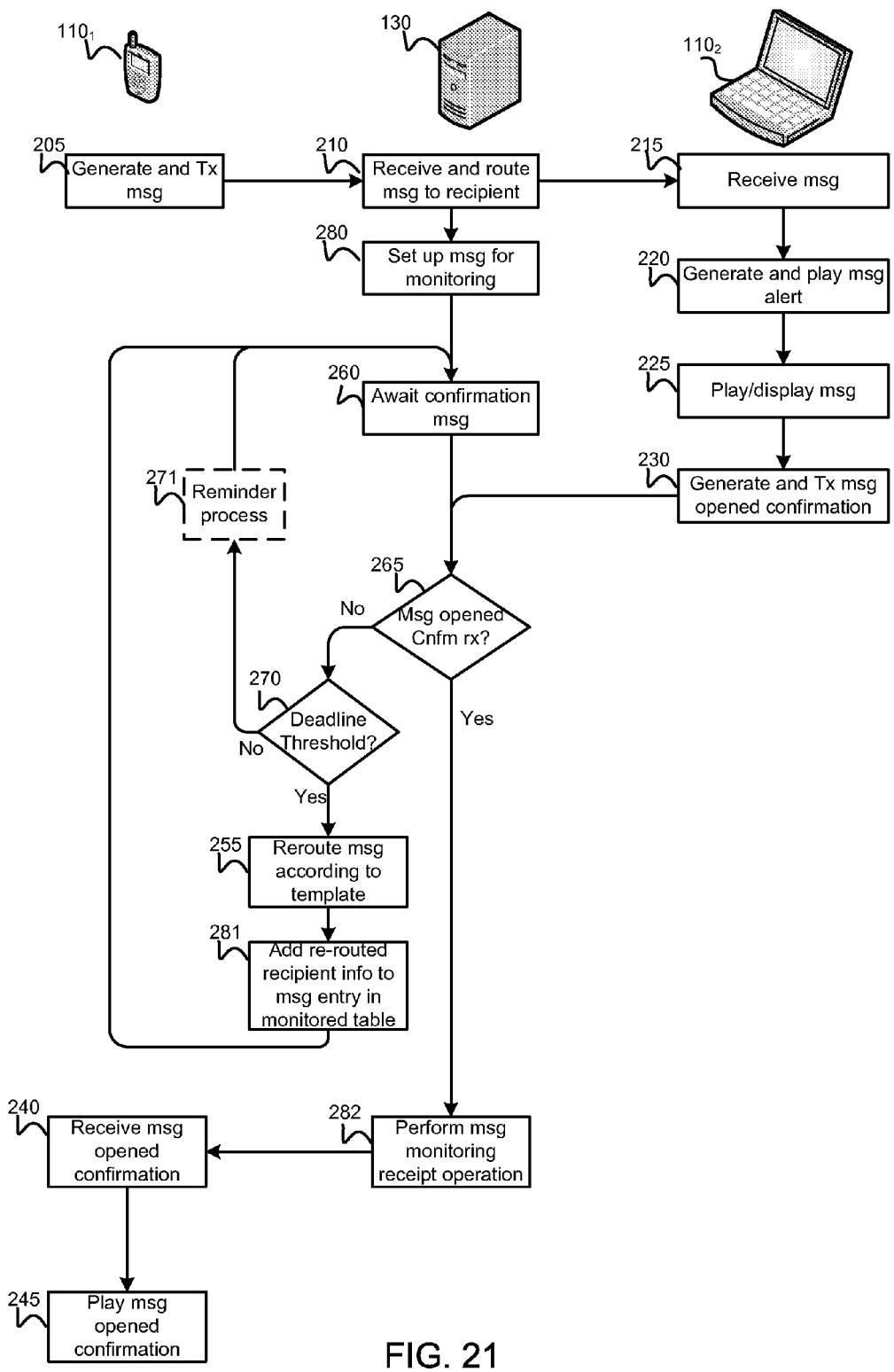
FIG. 21 is a process flow diagram of an embodiment method for re-routing a message when a sent message has not been read within a pre-determined time before a deadline and monitoring the message status to avoid duplicate responses.
Figure 22:
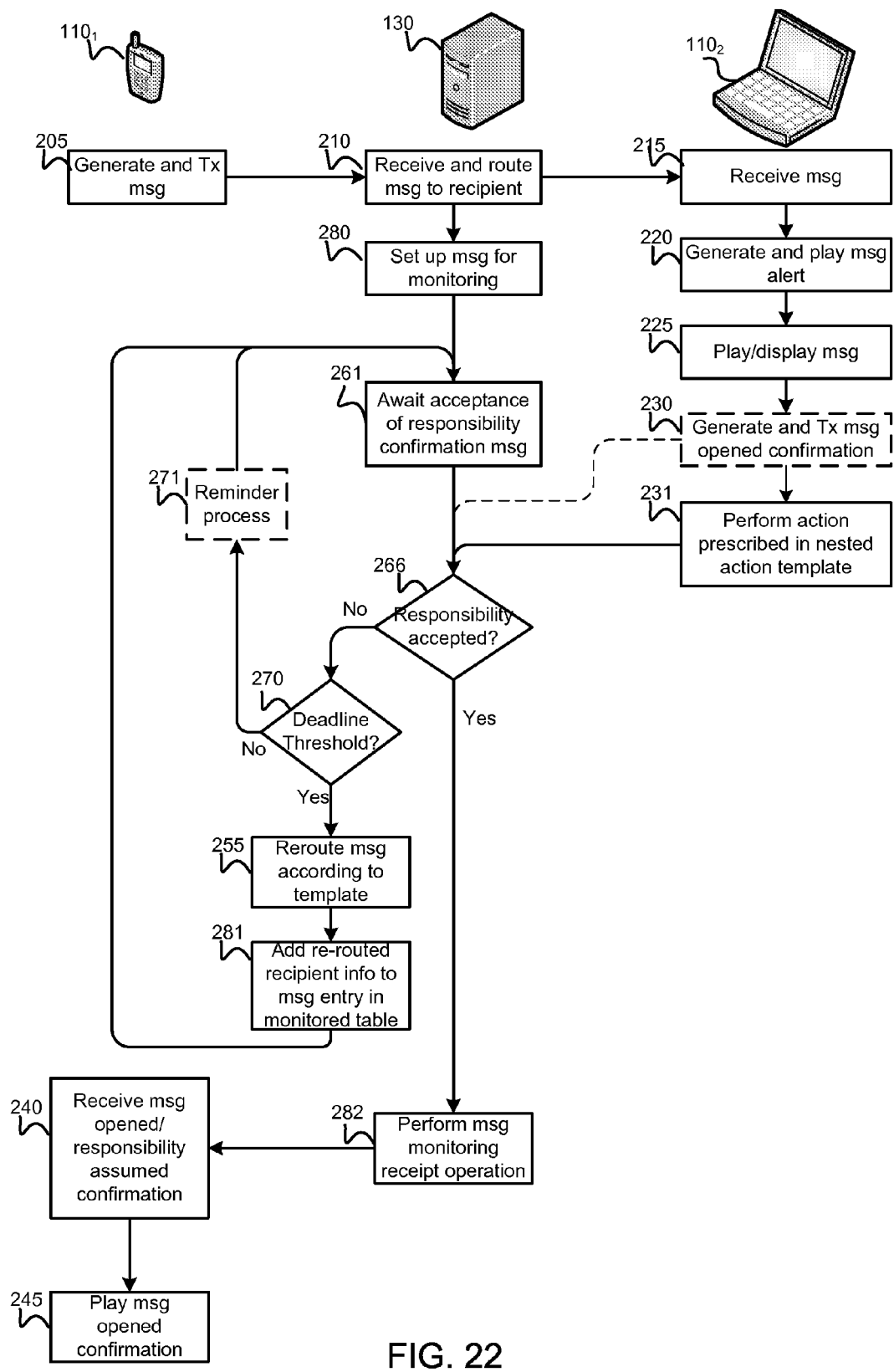
FIG. 22 is a process flow diagram of an alternative embodiment method for re-routing a message when an indication of acceptance of responsibility for a sent message has not been returned within a pre-determined time before a deadline and monitoring the message status to avoid duplicate responses.

FIG. 20 is a process flow diagram of an embodiment method for re-routing a message when an intended recipient is unavailable in an asynchronous mediated communication network including monitoring of the message status to avoid duplicate responses. FIG. 21 is a process flow diagram of an embodiment method for re-routing a message when a sent message has not been read within a pre-determined time before a deadline including monitoring of the message status to avoid duplicate responses. FIG. 22 is a process flow diagram of an embodiment method for re-routing a message when responsibility for a sent message has not been assumed by a recipient (original or re-routed) within a pre-determined time before a deadline including monitoring of the message status to avoid duplicate responses. The process flows shown in FIGS. 20-22 are similar to the process flows illustrated in FIGS. 3 and 4, so the foregoing descriptions of like numbered steps (205-255 and 260-271) apply to FIGS. 20-22.

When a message is sent from a sender's communication device $110_1$ to a recipient's communication device $110_{2-N}$, it is received and routed to the recipient(s) by the mediator 130 (see step 210, FIGS. 2, 4 and 9 above). In order to monitor the message, the mediator 130 may also perform steps to set up the message for monitoring, step 280. Steps involved in setting up the message for monitoring (step 280) are discussed in more detail below with respect to FIG. 23. Although FIGS. 20-22 depict performing step 280 subsequent to the routing of the message (step 210), the steps to set up the message for monitoring may be performed prior to, subsequent to or concurrently with the mediator 130 relaying of the message to the recipient's communication device $110_{2-N}$ (step 210).

In the event the message requires escalation and re-routing (step 255), the mediator may add information regarding the re-routed recipient(s) in a data entry in a monitoring table, step 281. When the mediator 130 has added the information regarding the re-routed recipient(s) to the monitoring table (step 281), the mediator 130 may return to step 260 and await a message opened confirmation message from a recipient.

FIG. 22 is a process flow diagram of an alternative embodiment method for re-routing a message when responsibility for acting upon a sent message has not been affirmatively received by the mediator 130 within a pre-determined time before a deadline. The alternative embodiment process flow illustrated in FIG. 22 is similar to the process flow illustrated in FIG. 21 except that an affirmative act on the part of the recipient to accept responsibility for the message is required. In the embodiments described above with reference to FIG. 21, it may be assumed that when a recipient opens a message the recipient tacitly accepts responsibility for the message and any follow actions necessitated by the original message. Thus, the return of the message opened confirmation is treated as an indication that the recipient has accepted responsibility for the original message. However, in the alternative embodiment illustrated in FIG. 22, it is presumed that recipients may open the original message but choose not to accept responsibility for taking the necessary actions, so an affirmative acceptance of responsibility is required before the message monitored receipt operation, step 282, may commence.

In the alternative embodiment illustrated in FIG. 22 the mediator 130 awaits an affirmative indication of acceptance of responsibility from a recipient, step 261. The affirmative indication of acceptance of responsibility may be a message back to the mediator 130 in which the recipient expressly accepts responsibility for the original message. For example, the message back could be an acceptance or affirmative response message, such as provided in some e-mail messaging systems (e.g., "voting buttons" in Microsoft Office®), or a written response message in which the recipient expressly assumes responsibility. Alternatively, the recipient may perform some other affirmative action that indicates the recipient's acceptance of responsibility or performance of an action required or requested by the message. For example, the recipient may perform one of the actions identified in a nested action template included in the original message. Alternatively, the recipient may perform some other actions, such as responding to the original sender. In any case, a message indicating that the affirmative action has been accomplished may be generated and sent to the mediator 130, step 231. Any of a variety of communication devices may send this message, and not just the recipient's communication device. For example, if a radiologist receives a message indicating an X-ray needs to be read and performs that task on a workstation, that workstation could generate and send the affirmative action message to the mediator 130. Upon receipt of the indication of acceptance of responsibility (i.e., determination 266=Yes), the mediator 130 may commence the message monitored receipt operation, step 282. In this manner, the original message will continue to be re-routed until a recipient (original or re-routed) affirmatively accepts responsibility for the original message and any action necessitated by the original message.

Rather than simply relaying the message opened confirmation (step 235 in FIGS. 3 and 4), in the embodiment methods illustrated in FIGS. 20-22, the mediator 130 may perform a message monitoring receipt operation, step 282. As discussed in more detail below with reference to FIG. 24, the mediator 130 may determine if multiple recipients have received the asynchronous message and generate a delete instruction message to each of the multiple recipients in addition to relaying the message opened confirmation to the original sender, step 235. The message monitoring receipt operation is described in more detail below with reference to FIG. 24. Although FIGS. 20-22 depict an embodiment method for monitoring the message status of a message that has been re-routed, the process flow illustrated in FIGS. 20-22 may also monitor the message status of a message that has not been re-routed. For example, if the original sender addressed the message to multiple recipients it may be desirable to monitor the message status to insure that only one of the multiple recipients responds to the message. Thus, by preparing the message for monitoring, steps 280 and 282, the mediator 130 may monitor when a message is responded to and take steps to avoid duplicate responses even when the message has not been re-routed.

Figure 23:
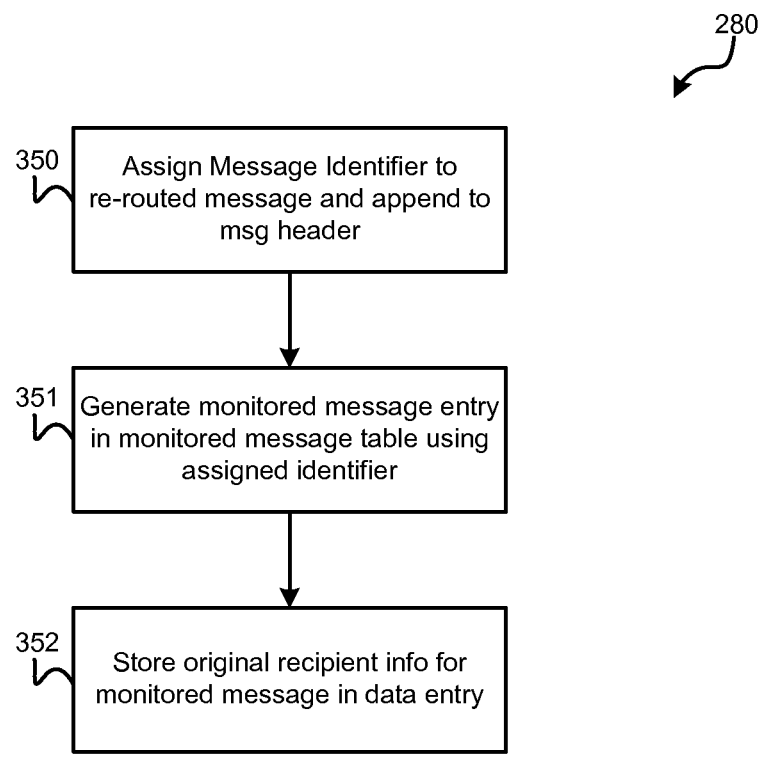
FIG. 23 is a process flow diagram of an embodiment method for setting up a message for monitoring.

FIG. 23 illustrates an embodiment method for setting up a message for monitoring. As discussed above with reference to FIGS. 20-22, when the mediator 130 receives and routes an asynchronous message (step 210) it may implement steps (step 280) which allow the mediator to monitor when any of the recipients (original or re-routed) provides a message opened confirmation, or affirmative indication of acceptance of responsibility, to the original sender. When an asynchronous message is initially received from a sender's communication device $110_1$ by the mediator 130 it may assign a message identifier to the asynchronous message and append the assigned message identifier to the asynchronous message header, step 350. The mediator 130 may also generate a data entry in a monitored message table for the asynchronous message, step 351. The data entry may include the assigned and appended message identifier. In addition, the mediator 130 may retrieve information regarding the original recipient(s) contained within the message header, including the address for each recipient's communication device. This information may be stored in a data field for original recipient(s) corresponding to the assigned message identifier in the monitored message table, step 352. The message identifier may be assigned sequentially or randomly. In addition, identifying information already contained in the original message header may be used as the assigned identifier for the data entry in the monitored message table. An example monitored message table is illustrated in FIG. 25 and discussed in more detail below.

In the event the asynchronous message is re-routed (step 255), the mediator 130 may add information regarding the re-routed recipient(s) to the monitored message table, step 281. In order to correctly add information regarding the re-routed recipient(s) to the appropriate data entry, each time the mediator 130 re-routes the asynchronous message the mediator 130 may retrieve the message identifier appended to the message header in step 350 and store the information in the monitored message table for the appropriate message identifier.

Figure 24:
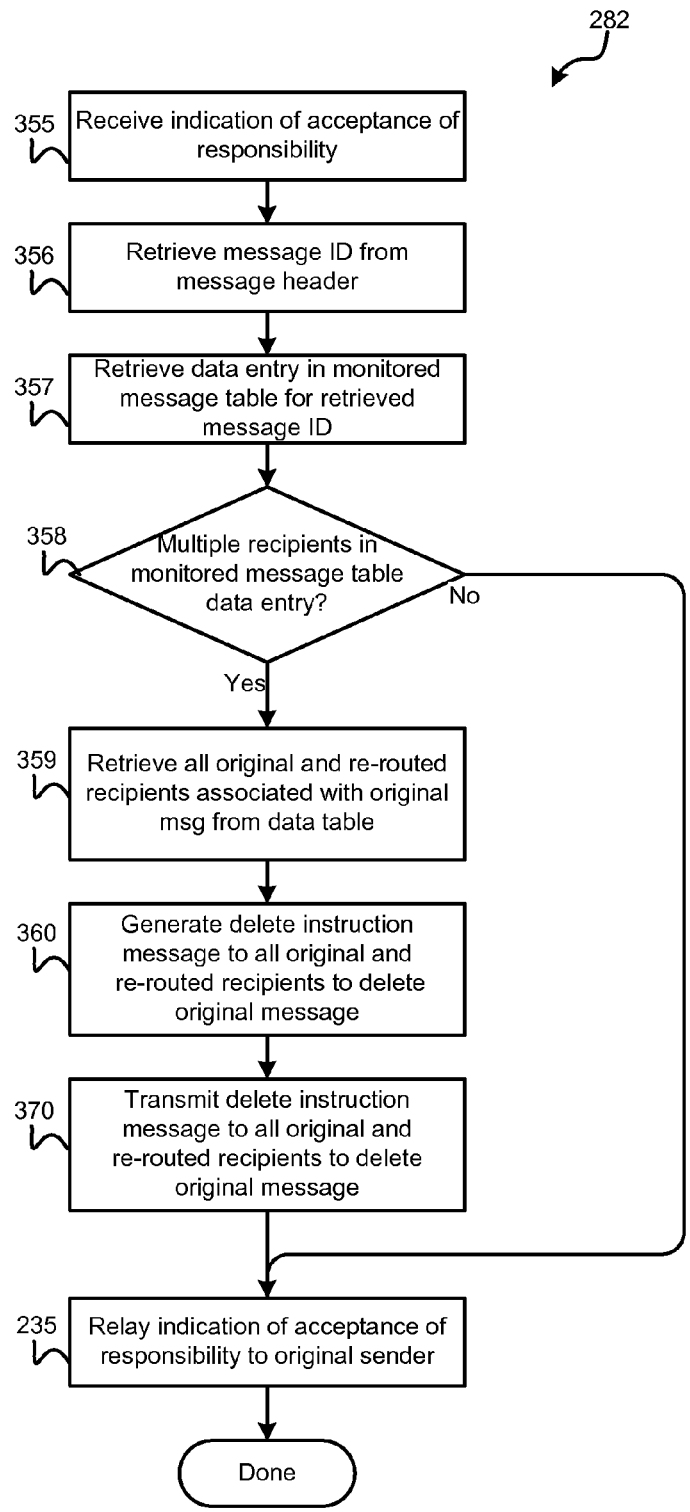
FIG. 24 is a process flow diagram of an embodiment method for monitoring the status of a re-routed message.

FIG. 24 illustrates an embodiment method for monitoring the status of re-routed messages. When the mediator 130 receives an indication (tacit or affirmative) of acceptance of responsibility for the original message any subsequent actions necessitated by the original message from a recipient, the mediator 130 may perform a message monitored receipt operation, step 282. As illustrated in FIG. 24, the message monitored receipt operation 282 may be initiated when the mediator 130 receives an indication of acceptance of responsibility from a recipient, step 355. The mediator 130 may retrieve the message identifier from the message header, step 356. Using the message identifier, the mediator may retrieve the corresponding data entry in the monitored message table, step 357. The mediator 130 may determine whether there are multiple recipients (original or re-routed) listed in the monitored message table corresponding to the identified message, determination 358. If there is only a single recipient listed in the monitored message table (i.e., determination 358=No), this indicates that the original sender sent the message to only one recipient and the message has not been re-routed. Accordingly, the message will only appear in the original recipient's message queue. Thus, there is no potential for duplicate. Consequently, the mediator 130 may relay the indication of acceptance of responsibility to the original sender, step 235, without further operations. As previously discussed, the indication of acceptance of responsibility may be a message opened confirmation or an affirmative indication of acceptance of responsibility.

If there are multiple recipients listed in the monitored message table data entry (i.e., determination 358=Yes), this indicates that either the original sender sent the message to multiple recipients or the message has been re-routed. Accordingly, the message will appear in multiple recipients' message queues. In order to avoid duplicate responses to the message and possible confusion, the mediator 130 may retrieve all of the original and re-routed recipients' address information listed in the monitored message table, step 359. The mediator 130 may also generate a delete instruction message and addressed to the retrieved recipient addresses, step 360. The mediator 130 may then transmit the delete instruction message to all original and re-routed recipients so that the asynchronous message will be deleted from all recipient message queues, step 370. The delete instruction message may be in the form of a short message service (SMS) message, multimedia message service (MMS), enhanced message service (EMS), email, or similar message type. Such a delete instruction message may be a recipient readable instruction message that informs the recipient that the asynchronous message has been acted upon and therefore may be manually deleted from the recipient's communication device message queue. Alternatively, the delete instruction message may be an executable instruction (e.g., an XML string) that causes the recipient communication device $110_{2-N}$ to find and delete the identified message from the recipients' message queues. The mediator 130 also may relay the message opened confirmation to the original sender, step 235. The mediator 130 may relay the indication of acceptance of responsibility to the original sender prior to, subsequent to, or concurrently with any of steps 359-360 and 370. Once the mediator 130 has relayed the indication of acceptance of responsibility to the original sender, the mediator 130 may await the next receive indication of acceptance of responsibility.

In an alternative embodiment (not shown), the mediator 130 may further transmit a message to all original and re-routed recipients that received the delete instruction indicating to the recipients that a message has been deleted from their respective message queues. The message may provide the recipients with some indication as to the contents of the deleted message and/or the reason for deletion. In this manner, recipients who may notice new messages in their message queues but did not open or read the received messages may be alerted to the automated deletion activity within their queues. Also, this embodiment enables recipients to learn who else has accepted responsibility for tasks, which may be useful in coordinating work flow and responsibilities.

FIG. 25 is an example of a monitored message table that may be suitable for use with an embodiment. The monitored message table may contain a plurality of data entries, one for each mediated message that has been routed through the mediator 130. Each monitored message data entry may be identified by a message identifier 400. The message identifier may be arbitrarily assigned by the mediator 130 or may be selected from retrieved information from the message header itself. In instances where the mediator 130 assigns an arbitrary message identifier, the assigned message identifier may be appended to the message header itself. Each data entry may also contain the original recipient information that was inputted by the sender. The original recipient address information 402 may be in the form of a recipient name or label that is to be correlated to any of the re-routing templates (e.g., such as are illustrated in FIGS. 14a-14c) to obtain actual communication device address information. Alternatively, the actual recipient address information may be listed in the monitored message table. Similarly, the re-routed recipient address information 404 may be in the form of a recipient name or label that may be correlated to any of the re-routing templates (e.g., such as are illustrated in FIGS. 14a-14c) to obtain communication device address information. Each time the message is re-routed the list of re-routed recipient address information may increase. In this manner, the mediator 130 may insure that all possible recipients of the message receive the delete instruction message. Thus, once a single recipient has responded to the original message, all other pending copies of the message may be deleted from other recipient communication devices $110_{2-N}$.

The embodiments described above may be implemented on any of a variety of communication devices, such as, for example, cellular telephones, personal data assistants (PDA) with cellular telephone and/or WIFI transceivers, mobile electronic mail receivers, mobile web access devices, laptop computers, palmtop computers and other processor-equipped devices. In addition, the various embodiments disclosed herein may be implemented by any processor-equipped device including stationary desktop computers. Typically, such portable computing devices will have in common the components illustrated in FIG. 26. For example, the communication device 110 may include a processor 191 coupled to internal memory 192 and a display 11. Additionally, the communication device 110, 180 may have an antenna 194 for sending and receiving electromagnetic radiation that is connected to a wireless data link and/or cellular telephone transceiver 195 coupled to the processor 191. In some implementations, the transceiver 195 and portions of the processor 191 and memory 192 used for cellular telephone communications is referred to as the air interface since it provides a data interface via a wireless data link. Communication devices 10 also typically include a key pad 13 or miniature keyboard and menu selection buttons or rocker switches 12 for receiving user inputs. The processor 191 may further be connected to a vocoder 199 which is in turn connected to a microphone 19 and speaker 18. The communication device 110 may also include a wired network interface 194, such as a universal serial bus (USB) or FireWire® connector socket, for connecting the processor 191 to an external computing device such as a personal computer or external local area network.

The processor 191 may be any programmable microprocessor, microcomputer or multiple processor chip or chips that can be configured by software instructions (applications) to perform a variety of functions, including the functions of the various embodiments described above. In one aspect, the processor 191 implements the software stored in the memory 192 to execute one of more of the features of the AMC system, including but not limited to, role-based message routing, manual or automatic message redirection, mediated broadcast including one-to-many communication, real time deadline modification, implementation of priority levels using deadlines, dynamic reminders, verbosity control, etc. In some communication devices 110, multiple processors 191 may be provided, such as one processor dedicated to wireless communication functions and one processor dedicated to running other applications. Typically, software applications may be stored in the internal memory 192 before they are accessed and loaded into the processor 191. In some communication devices 110, 180, the processor 191 may include internal memory sufficient to store the application software instructions. For the purposes of this description, the term memory refers to all memory accessible by the processor 191, including internal memory 192 and memory within the processor 191 itself. In many communication devices 10, the memory 192 may be a volatile or nonvolatile memory, such as flash memory, or a mixture of both.

Figure 27:
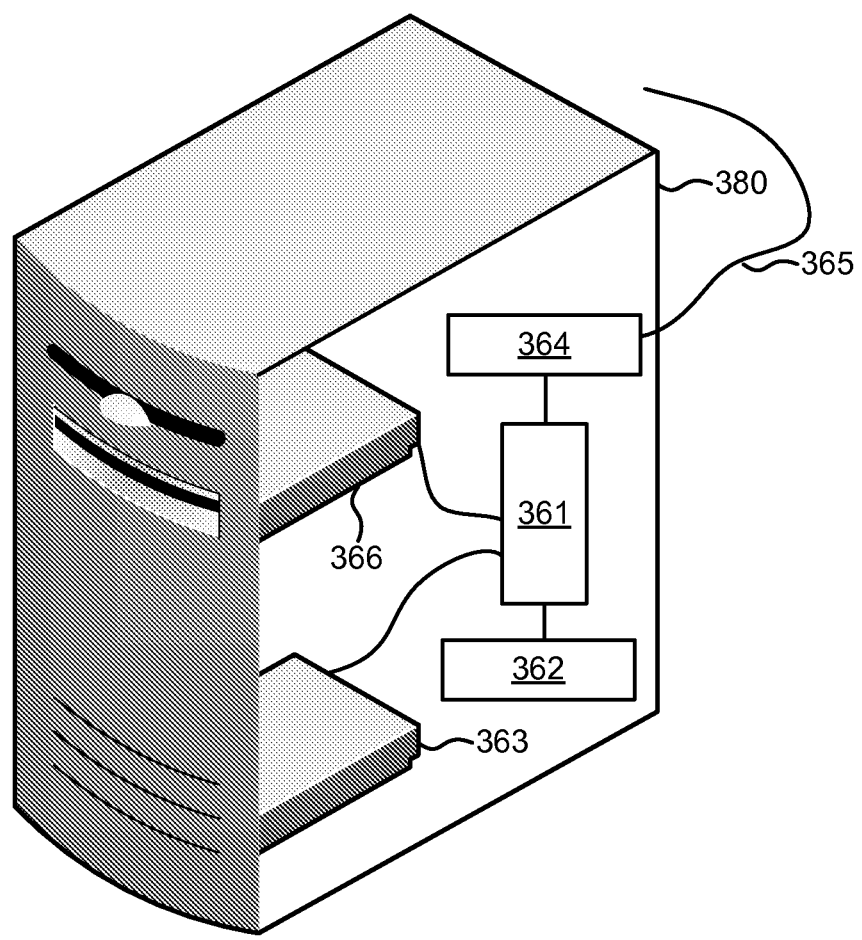
FIG. 27 is a component block diagram of an example remote server suitable for use with the various embodiments.

A number of the embodiments described above may also be implemented with any of a variety of remote server devices acting as a mediator 130, such as the server 380 illustrated in FIG. 27. Such a remote server 380 typically includes a processor 361 coupled to volatile memory 362 and a large capacity nonvolatile memory, such as a disk drive 363. The server 380 may also include a floppy disc drive and/or a compact disc (CD) drive 366 coupled to the processor 361. Typically, the server 380 may also include a user input device like a keyboard (not shown) and a display (not shown). The server 380 may also include a number of connector ports coupled to the processor 361 for establishing data connections or receiving external memory devices, such as USB or FireWire® connector sockets or other network connection circuits 365 for coupling the processor 361 to a network 205.

Thus, the advantages of the asynchronous mediated communication method and apparatus disclosed herein include the ability to set priority levels for messages according to deadlines which in turn may depend on the message content or user designation. In one aspect, a user sets the message deadlines. An additional advantage includes modifying the message deadlines based on the communication needs (e.g., the message content). Role based, and not person-based, routing of messages is part of the advantages. Delegation of roles, which could include manual and/or automatic re-routing of messages, as well as escalation of messages based on the need are all part of the advantages of asynchronous mediated communication method and apparatus disclosed herein.

In much of the description, reference is made to the healthcare industry. However, the healthcare industry is one example and the concept disclosed may be implemented in other applications without affecting the spirit or scope of the disclosure. Therefore, it should be noted that the description herein illustrate examples for the purposes of explanation. The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order.

The hardware used to implement the foregoing embodiments may be processing elements and memory elements configured to execute a set of instructions, including microprocessor units, microcomputer units, programmable floating point gate arrays (FPGA), and application specific integrated circuits (ASIC) as would be appreciated by one of skill in the art, wherein the set of instructions are for performing method steps corresponding to the above methods. Alternatively, some steps or methods may be performed by circuitry that is specific to a given function.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. The software module may reside in a processor readable storage medium and/or processor readable memory both of which may be any of RAM memory, flash memory, ROM memory, EPROM memory, EEPROM memory, registers, hard disk, a removable disk, a CD-ROM, or any other tangible form of data storage medium known in the art. Moreover, the processor readable memory may comprise more than one memory chip, memory internal to the processor chip, in separate memory chips, and combinations of different types of memory such as flash memory and RAM memory. References herein to the memory of a mobile handset are intended to encompass any one or all memory modules within the mobile handset without limitation to a particular configuration, type or packaging. An exemplary storage medium is coupled to a processor in either the mobile handset or the theme server such that the processor can read information from, and write information to, the storage medium. In the alternative, the storage medium may be integral to the processor. The processor and the storage medium may reside in an ASIC.

The foregoing description of the various embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein, and instead the claims should be accorded the widest scope consistent with the principles and novel features disclosed herein.

What is claimed is:

1. A method for monitoring asynchronous messages, comprising:
   receiving an asynchronous message intended for at least one first recipient from a sender's communication device;
   assigning a message identifier to the received asynchronous message in a monitored message table;
   appending the message identifier to a header of the asynchronous message header, wherein the asynchronous message header comprises a data field with information identifying a role performed by the at least one first recipient;
   storing information for all recipients of the message in the monitored message table corresponding to the assigned message identifier;
   routing the asynchronous message to the at least one first recipient's communication device; and
   re-routing the asynchronous message to at least one second recipient's communication device if an indication of acceptance of responsibility is not received from the at least one first recipient's communication device within a pre-determined deadline, wherein the re-routing is performed according to a routing template and a dynamic availability table,
   wherein:
      the routing template comprises entries that each have a potential recipient of the asynchronous message, an associated role performed by the potential recipient, and a priority rank within the associated role for the potential recipient; and
      re-routing the asynchronous message is based on availability of potential recipients having an associated role that is equal to the role performed by the at least one first recipient.

2. The method of claim 1, further comprising:
   determining whether the asynchronous message was addressed to more than one first recipient's communication device;
   determining whether an indication of acceptance of responsibility is received from a responsive first recipient's communication device; and
   transmitting a delete instruction message to a non-responsive first recipient's communication devices if it is determined that the asynchronous message was addressed to more than one first recipient's communication device and that an indication of acceptance of responsibility is received from a responsive first recipient's communication device.

3. The method of claim 2, wherein determining if the asynchronous message was addressed to more than one first recipient's communication device comprises:
   retrieving the message identifier for the asynchronous message; and
   recalling information stored in the monitored message table.

4. The method of claim 2, wherein the delete instruction message is an executable instruction that automatically deletes the asynchronous message from all recipients' message queues upon receipt.

5. The method of claim 2, wherein the delete instruction message is a recipient readable instruction message informing the recipient that the asynchronous message may be deleted from the recipient's message queue.

6. The method of claim 1, wherein the indication of acceptance of responsibility comprises a message open confirmation.

7. The method of claim 1, wherein the indication of acceptance of responsibility comprises an affirmative acceptance of responsibility message.

8. A mediator device for mediating asynchronous message routing, comprising:
    means for receiving an asynchronous message intended for at least one first recipient from a sender's communication device;
    means for assigning a message identifier to the received asynchronous message in a monitored message table;
    means for appending the message identifier to a header of the asynchronous message, wherein the asynchronous message header comprises a data field with information identifying a role performed by the at least one first recipient;
    means for storing information for all recipients of the message in the monitored message table corresponding to the assigned message identifier;
    means for routing the asynchronous message to the at least one first recipient's communication device; and
    means for re-routing the asynchronous message to at least one second recipient's communication device if an indication of acceptance of responsibility is not received from the at least one first recipient's communication device within a pre-determined deadline, wherein the re-routing is performed according to a routing template and a dynamic availability table
    wherein:
        the routing template comprises entries that each have a potential recipient of the asynchronous message, an associated role performed by the potential recipient, and a priority rank within the associated role for the potential recipient; and
        means for re-routing the asynchronous message comprises means for re-routing the asynchronous message based on availability of potential recipients having an associated role that is equal to the role performed by the at least one first recipient.

9. The mediator device of claim 8, further comprising:
    means for determining whether the asynchronous message was addressed to more than one first recipient's communication device;
    means for determining whether an indication of acceptance of responsibility is received from a responsive first recipient's communication device; and
    means for transmitting a delete instruction message to a non-responsive first recipient's communication devices if it is determined that the asynchronous message was addressed to more than one first recipient's communication device and that an indication of acceptance of responsibility is received from a responsive first recipient's communication device.

10. The mediator device of claim 9, wherein means for determining if the asynchronous message was addressed to more than one first recipient's communication device comprises:
    means for retrieving the message identifier for the asynchronous message; and
    means for recalling information stored in the monitored message table.

11. The mediator device for mediating asynchronous message routing of claim 9, wherein the delete instruction message is an executable instruction that automatically deletes the asynchronous message from all recipients' message queues upon receipt.

12. The mediator device for mediating asynchronous message routing of claim 9, wherein the delete instruction message is a recipient readable instruction message informing the recipient that the asynchronous message may be deleted from the recipient's message queue.

13. The mediator device for mediating asynchronous message routing of claim 9, wherein the indication of acceptance of responsibility comprises a message open confirmation.

14. The mediator device for mediating asynchronous message routing of claim 9, wherein the indication of acceptance of responsibility comprises an affirmative acceptance of responsibility message.

15. A mediator server for mediating asynchronous message routing, comprising:
    a memory unit; and
    a processor coupled to the memory unit, wherein the processor is configured with software instructions to perform steps comprising:
        receiving an asynchronous message intended for at least one first recipient from a communication device;
        assigning a message identifier to the received asynchronous message in a monitored message table;
        appending the message identifier to a header of the asynchronous message, wherein the asynchronous message header comprises a data field with information identifying a role performed by the at least one first recipient;
        storing information for all recipients of the message in the monitored message table corresponding to the assigned message identifier;
        routing the asynchronous message to the at least one first recipient's communication device; and
        re-routing the asynchronous message to at least one second recipient's communication device if an indication of acceptance of responsibility is not received from the at least one first recipient's communication device within a pre-determined deadline, wherein the re-routing is performed according to a routing template and a dynamic availability table, wherein:
            the routing template comprises entries that each have a potential recipient of the asynchronous message, an associated role performed by the potential recipient, and a priority rank within the associated role for the potential recipient; and
            re-routing the asynchronous message is based on availability of potential recipients having an associated role that is equal to the role performed by the at least one first recipient.

16. The mediator server of claim 15, wherein the processor is configured with software instructions to perform steps further comprising:
    determining whether the asynchronous message was addressed to more than one first recipient's communication device;
    determining whether an indication of acceptance of responsibility is received from a responsive first recipient's communication device; and
    transmitting a delete instruction message to a non-responsive first recipient's communication devices if it is determined that the asynchronous message was addressed to more than one first recipient's communication device and that an indication of acceptance of responsibility is received from a responsive first recipient's communication device.

17. The mediator server of claim 16, wherein the processor is configured with software instructions to perform steps further comprising:
retrieving the message identifier for the asynchronous message; and
recalling information stored in the monitored message table.

18. The mediator server of claim 16, wherein the delete instruction message is an executable instruction that automatically deletes the asynchronous message from all recipients' message queues upon receipt.

19. The mediator server of claim 16, wherein the delete instruction message is a recipient readable instruction message informing the recipient that the asynchronous message may be deleted from the recipient's message queue.

20. The mediator server of claim 15, wherein the indication of acceptance of responsibility comprises a message open confirmation.

21. The mediator server of claim 15, wherein the indication of acceptance of responsibility comprises an affirmative acceptance of responsibility message.

22. A non-transitory processor-readable storage medium having stored thereon processor-executable software instructions configured to cause a processor to perform steps comprising:
receiving an asynchronous message intended for at least one first recipient from a sender's communication device;
assigning a message identifier to the received asynchronous message in a monitored message table;
appending the message identifier to a header of the asynchronous message header, wherein the asynchronous message header comprises a data field with information identifying a role performed by the at least one first recipient;
storing information for all recipients of the message in the monitored message table corresponding to the assigned message identifier;
routing the asynchronous message to the at least one first recipient's communication device; and
re-routing the asynchronous message to at least one second recipient's communication device if an indication of acceptance of responsibility is not received from the at least one first recipient's communication device within a pre-determined deadline, wherein the re-routing is performed according to a routing template and a dynamic availability table, wherein:
the routing template comprises entries that each have a potential recipient of the asynchronous message, an associated role performed by the potential recipient, and a priority rank within the associated role for the potential recipient; and
re-routing the asynchronous message is based on availability of potential recipients having an associated role that is equal to the role performed by the at least one first recipient.

23. The non-transitory processor-readable storage medium of claim 22, wherein the stored software instructions are configured to cause a processor to perform steps further comprising:
determining whether the asynchronous message was addressed to more than one first recipient's communication device;
determining whether an indication of acceptance of responsibility is received from a responsive first recipient's communication device; and
transmitting a delete instruction message to a non-responsive first recipient's communication devices if it is determined that the asynchronous message was addressed to more than one first recipient's communication device and that an indication of acceptance of responsibility is received from a responsive first recipient's communication device.

24. The non-transitory processor-readable storage medium of claim 23, wherein the stored software instructions are configured to cause a processor to perform steps further comprising:
retrieving the message identifier for the asynchronous message; and
recalling information stored in the monitored message table.

25. The non-transitory processor-readable storage medium of claim 23, wherein the stored the stored software instructions are configured to perform steps such that the delete instruction message is an executable instruction that automatically deletes the asynchronous message from all recipients' message queues upon receipt.

26. The non-transitory processor-readable storage medium of claim 23, wherein the stored the stored software instructions are configured to perform steps such that the delete instruction message is a recipient readable instruction message informing the recipient that the asynchronous message may be deleted from the recipient's message queue.

27. The non-transitory processor-readable storage medium of claim 22, wherein the stored the stored software instructions are configured to perform steps such that the indication of acceptance of responsibility comprises a message open confirmation.

28. The non-transitory processor-readable storage medium of claim 22, wherein the stored the stored software instructions are configured to perform steps such that the indication of acceptance of responsibility comprises an affirmative acceptance of responsibility message.

29. An asynchronous communication system, comprising:
an asynchronous communication network;
a first sender communication device linked to the asynchronous communication network, wherein the first sender communication device is configured to send asynchronous messages via the asynchronous communication network;
a first recipient communication device linked to the asynchronous communication network, wherein the first recipient communication device is configured to receive asynchronous messages via the asynchronous communication network and transmit a confirmation to the first sender communication device when a message received from the first sender communication device is opened; and
a mediator linked asynchronous communication network, wherein the mediator is configured to:
determine when an indication of acceptance of responsibility is sent from the first recipient communication device to the first sender communication device in response to the asynchronous message;
assign a message identifier to the asynchronous message in a monitored message table;
append the message identifier to a header of the asynchronous message, wherein the asynchronous message header comprises a data field with information identifying a role performed by at least one first recipient;

store information for all recipients of the asynchronous message in the monitored message table corresponding to the assigned message identifier; and re-route the asynchronous message to a second recipient communication device when it is determined that an indication of acceptance of responsibility is not received from the first recipient communication device within a pre-determined deadline, wherein the re-routing is performed according to a routing template and a dynamic availability table, wherein:

the routing template comprises entries that each have a potential recipient of the asynchronous message, an associated role performed by the potential recipient, and a priority rank within the associated role for the potential recipient; and the mediator is further configured to re-route the asynchronous message based on availability of potential recipients having an associated role that is equal to the role performed by the at least one first recipient.

30. The asynchronous communication system of claim 29, wherein the mediator is further configured to transmit a delete instruction message to all recipients of the asynchronous message whenever the mediator determines that the indication of acceptance of responsibility is sent.

31. The asynchronous communication system of claim 30, wherein the first and second recipient communication devices are capable of finding and deleting the asynchronous message from their message queues upon receipt of the delete instruction message.

32. The asynchronous communication system of claim 29, wherein the first and second recipient communication devices are capable of automatically generating the indication of acceptance of responsibility upon opening the asynchronous message.

33. The asynchronous communication system of claim 29, wherein the indication of acceptance of responsibility comprises a message open confirmation.

34. The asynchronous communication system of claim 29, wherein the indication of acceptance of responsibility comprises an affirmative acceptance of responsibility message.

* * * * *